US009045557B2

(12) United States Patent
Tsunoda et al.

(10) Patent No.: US 9,045,557 B2
(45) Date of Patent: Jun. 2, 2015

(54) NEIL3 PEPTIDES AND VACCINES INCLUDING THE SAME

(75) Inventors: Takuya Tsunoda, Kanagawa (JP); Ryuji Ohsawa, Kanagawa (JP); Sachiko Yoshimura, Kanagawa (JP); Tomohisa Watanabe, Kanagawa (JP); Yusuke Nakamura, Tokyo (JP); Yoichi Furukawa, Tokyo (JP)

(73) Assignee: ONCOTHERAPY SCIENCE, INC., Kanagawa (JP)

( * ) Notice: Subject to any disclaimer, the term of this patent is extended or adjusted under 35 U.S.C. 154(b) by 814 days.

(21) Appl. No.: 13/256,580

(22) PCT Filed: Mar. 15, 2010

(86) PCT No.: PCT/JP2010/001808
§ 371 (c)(1),
(2), (4) Date: Dec. 28, 2011

(87) PCT Pub. No.: WO2010/106770
PCT Pub. Date: Sep. 23, 2010

(65) Prior Publication Data
US 2012/0093845 A1    Apr. 19, 2012

Related U.S. Application Data

(60) Provisional application No. 61/210,512, filed on Mar. 18, 2009.

(51) Int. Cl.
*A61K 38/00* (2006.01)
*C07K 14/47* (2006.01)
*A61K 39/00* (2006.01)

(52) U.S. Cl.
CPC ............. *C07K 14/4748* (2013.01); *A61K 39/00* (2013.01)

(58) Field of Classification Search
None
See application file for complete search history.

(56) References Cited

U.S. PATENT DOCUMENTS

| 7,745,391 B2 * | 6/2010 | Mintz et al. ................. 514/19.3 |
| 2003/0109690 A1 * | 6/2003 | Ruben et al. ................. 536/23.1 |
| 2005/0196754 A1 * | 9/2005 | Drmanac et al. ................. 435/6 |
| 2006/0216301 A1 | 9/2006 | Tahara et al. |

FOREIGN PATENT DOCUMENTS

| CN | 1694901 A | 11/2005 |
| JP | 2006-052216 A | 2/2006 |
| WO | 03/104275 A2 | 12/2003 |
| WO | WO 2004/024766 A1 | 3/2004 |
| WO | 2007/047796 | * 4/2007 |
| WO | WO 2008/156827 A2 | 12/2008 |

OTHER PUBLICATIONS

Engelhard, Current Opinion in Immunology vol. 6 p. 13 (1994).*
Guo, et al Nature vol. 360 p. 384 (1992).*
Shastri et al J. Immunol. vol. 1995 vol. 155 p. 4339.*
Lin et al., "Functional assays of HLA A2-restricted epitope variant of latent membrane protein 1 (LMP-1) of Epstein-Barr virus in nasopharyngeal carcinoma of Southern China and Taiwan", *J. Biomed. Sci.*, 12:925-936 (2005).
Stevanovic, "Identification of Tumour-Associated T-Cell Epitopes for Vaccine Development", *Nat Rev Cancer*, 2(7):514-520 (2002).
NCBI GenBank Accession No. NM_018248, "Homo sapiens nei endonuclease VIII-like 3 (*E. coli*) (NEIL3), mRNA," 3 pgs. (Sep. 20, 2007).
Ishizaki, et al., "Inhibition of Tumor Growth with Antiangiogenic Cancer Vaccine Using Epitope Peptides Derived from Human Vascular Endothelial Growth Factor Receptor 1," *Clin Cancer Res.*, vol. 12(19), pp. 5841-5849 (Oct. 1, 2006).
Bandaru, et al., "A novel human DNA glycosylase that removes oxidative DNA damage and is homologous to *Escherichia coli* endonuclease VIII," *DNA Repari (AMST.)*, vol. 1(7), pp. 517-529 (Jul. 17, 2002).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Coulie, et al., "Cytolytic T-cell responses of cancer patients vaccinated with a MAGE antigen," *Immunol Rev.*, vol. 188, pp. 33-42 (Oct. 2002).
Fujie, et al., "A *MAGE*-1-Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Kikuchi, et al., "Identification of a SART-1-Derived Peptide Capable of Inducing HLA-A24-Restricted and Tumor-Specific Cytotoxic T Lymphocytes," *Int J Cancer*, vol. 81(3), pp. 459-466 (May 5, 1999).
Oiso, et al., "A Newly Identified *MAGE*-3-Derived Epitope Recognized by HLA-A24-Restricted Cytotoxic T Lymphocytes," *Int J Cancer*, vol. 81(3), pp. 387-394 (May 5, 1999).
Rosenberg, et al., "Cancer immunotherapy: moving beyond current vaccines," *Nat Med.*, vol. 10(9), pp. 909-915 (Sep. 2004).

(Continued)

*Primary Examiner* — Sheela J Huff
(74) *Attorney, Agent, or Firm* — Kilpatrick Townsend & Stockton LLP

(57) ABSTRACT

The present invention provides isolated peptides or the fragments derived from SEQ ID NO: 45, which bind to an HLA antigen and induce cytotoxic T lymphocytes (CTL). The peptides may include the above mentioned amino acid sequence with substitution deletion, or addition of one, two, or several amino acids sequences. The invention also provides pharmaceutical compositions including these peptides. The peptides of this invention can be used for diagnosing or treating cancer.

8 Claims, 10 Drawing Sheets

(56) References Cited

OTHER PUBLICATIONS

Strausberg, et al., GenBank: AAH25954.1 (http://www.ncbi.nlm.nih.gov/protein/AAH25954), 2 pages, retrieved Feb. 23, 2012 (Jul. 15, 2006).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), fl.pp. 4465-4468 (Oct. 15, 1997).

Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

NCBI Accession No. GDS825, 2 pages (Apr. 12, 2004, Search: May 6, 2010).

NCBI Accession No. GDS756, 2 pages (Apr. 20, 2004, Search: May 6, 2010).

NCBI Accession No. GDS1439, 2 pages (Sep. 20, 2005, Search: May 6, 2010).

Adams, et al. "Prediction of binding to MHC class I molecules," *J Immunol Methods*, vol. 185(2), pp. 181-190 (Sep. 25, 1995).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 2003).

Falk, et al., "Allele-specific motifs revealed by sequencing of self-peptides eluted from MHC molecules," *Nature*, vol. 351(6324), pp. 290-296 (May 23, 1991).

Hoffmann, et al., "The Ability of Variant Peptides to Reverse the Nonresponsiveness of T Lymphocytes to the Wild-Type Sequence p53$_{264-272}$ Epitope " *J Immunol.*, vol. 168(3), pp. 1338-1347 (Feb. 1, 2002).

Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).

Kubo, et al., "Definition of Specific Peptide Motifs for Four Major HLA-A Alleles," *J Immunol.*, vol. 152(8), pp. 3913-3924 (Apr. 15, 1994).

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).

Rammensee, et al., "MHC ligands and peptide motifs: first listing," *Immunogenetics*, vol. 41(4), pp. 178-228.

Schueler-Furman, et al., "Structure-based prediction of binding peptides to MHC class I molecules: Application to a broad range of MHC alleles," *Protein Sci.*, vol. 9(9), pp. 1838-1846 (Sep. 2000).

Zaremba, et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).

Roitt et al., Immunology, 2000, pp. 159-163.

Corresponding English document of Roitt et al., Immunology, 2000, 159-163 (pp. 114-117).

Marsh et al., The HLA FactsBook, San Diego: Academic Press, 2000, pp. 105 & 121.

Prevost et al., "Tumor-Infiltrating Lymphocytes Exhibiting High Ex Vivo Cytolytic Activity Fail to Prevent Murine Melanoma Tumor Growth in Vivo," *J. Immunol*, 1998, vol. 161, pp. 2187-2194.

Tan et al., "Rapid Death of Adoptively Transferred T Cells in Acquired Immunodeficiency Syndrome", *Blood*, 1999, vol. 93, No. 5, pp. 1506-1510.

Blohm et al., "Lack of Effector Cell Function and Altered Tetramer Binding of Tumor-Infiltrating Lymphocytes", *J Immunol* 2002; vol. 169, pp. 5522-5530.

Harlow et al., Antibodies. A Laboratory Manual, Cold Spring Harbor Laboratory Press. vol. 60, pp. 79-80 (1998).

Torisu et al., "Hematopoietic Tissue-Specific Expression of Mouse Neil3 for Endonuclease VIII-Like Protein", *J Biochem*, vol. 138, No. 6, pp. 763-772.

White et al., "Production and Characterization of T Cell Hybridomas", *Methods Mol Biol*, vol. 134, pp. 185-193 (2000).

* cited by examiner

Fig. 2-2
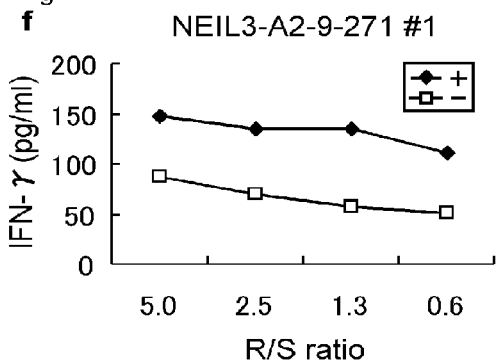
f  NEIL3-A2-9-271 #1
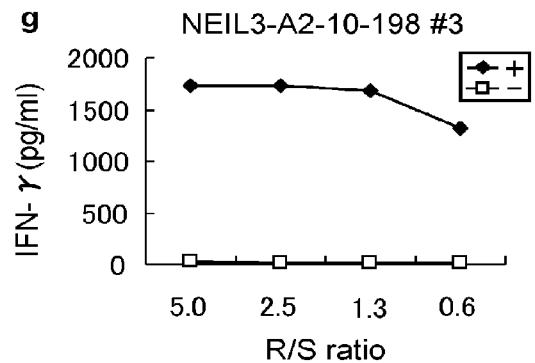
g  NEIL3-A2-10-198 #3
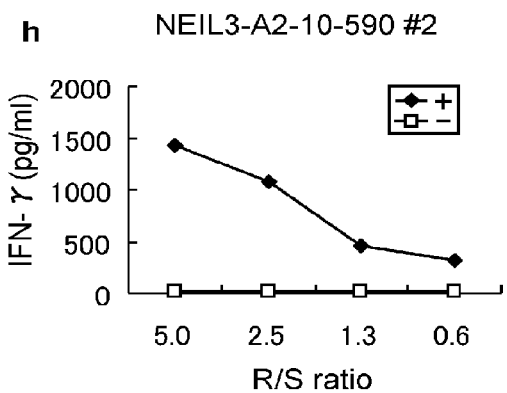
h  NEIL3-A2-10-590 #2
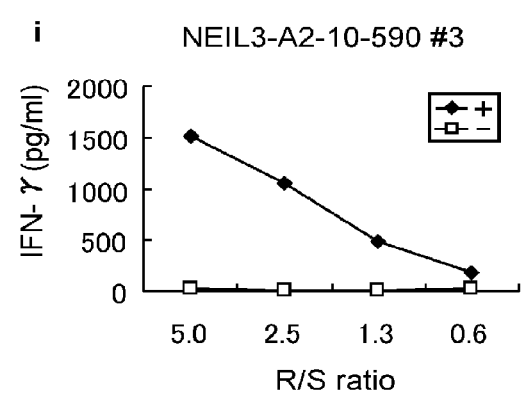
i  NEIL3-A2-10-590 #3
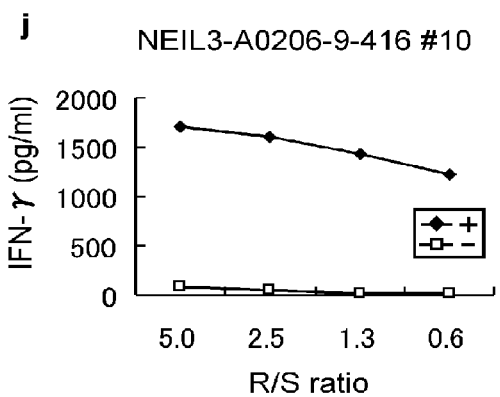
j  NEIL3-A0206-9-416 #10
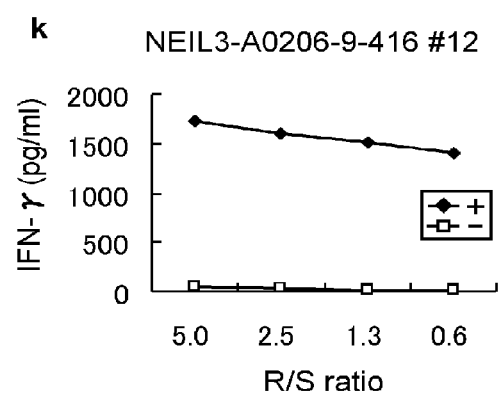
k  NEIL3-A0206-9-416 #12

Fig. 4-1
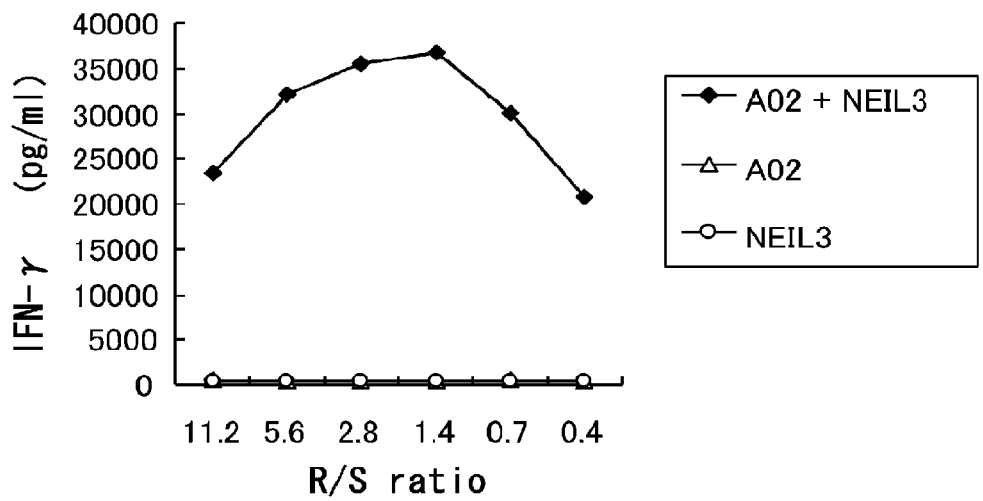
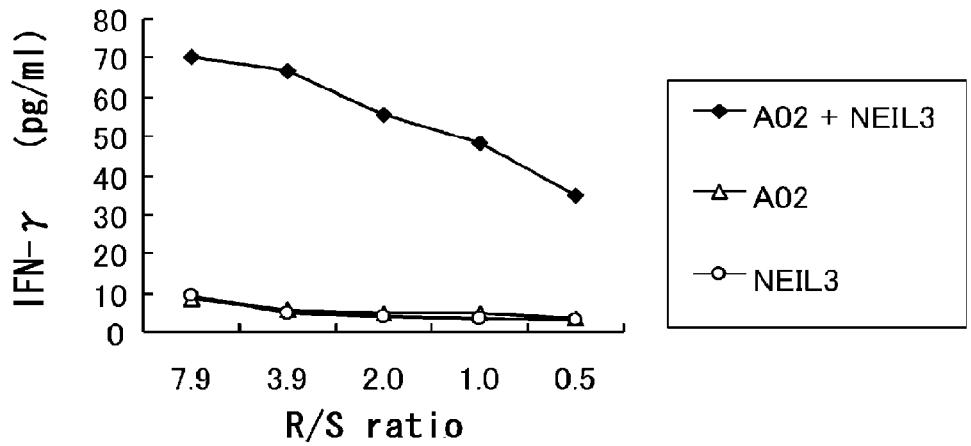
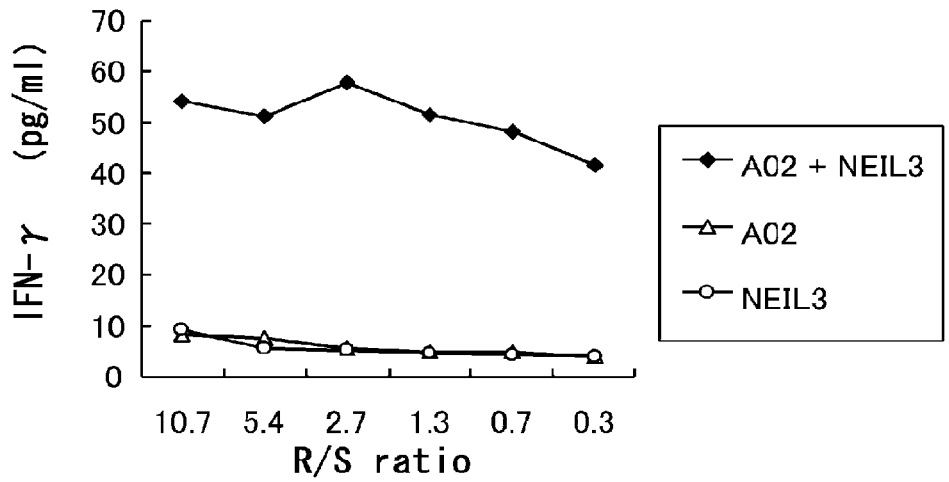

d

Fig. 5
a
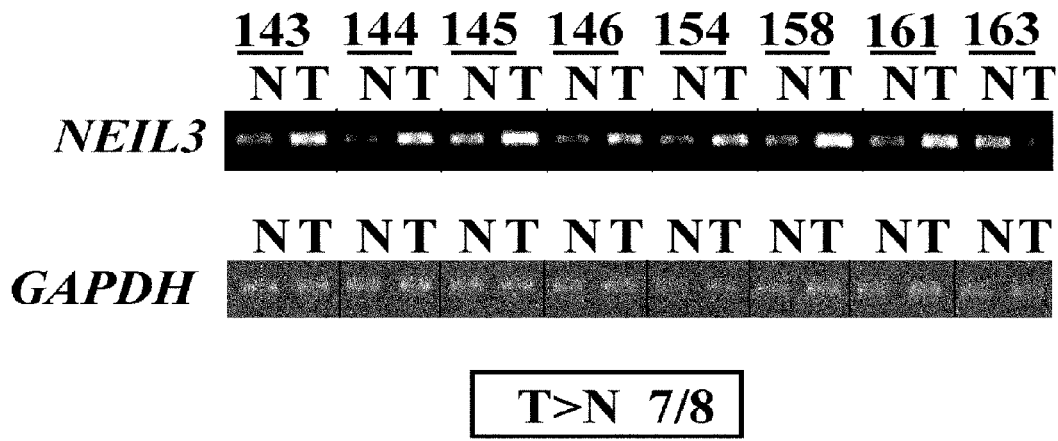
b
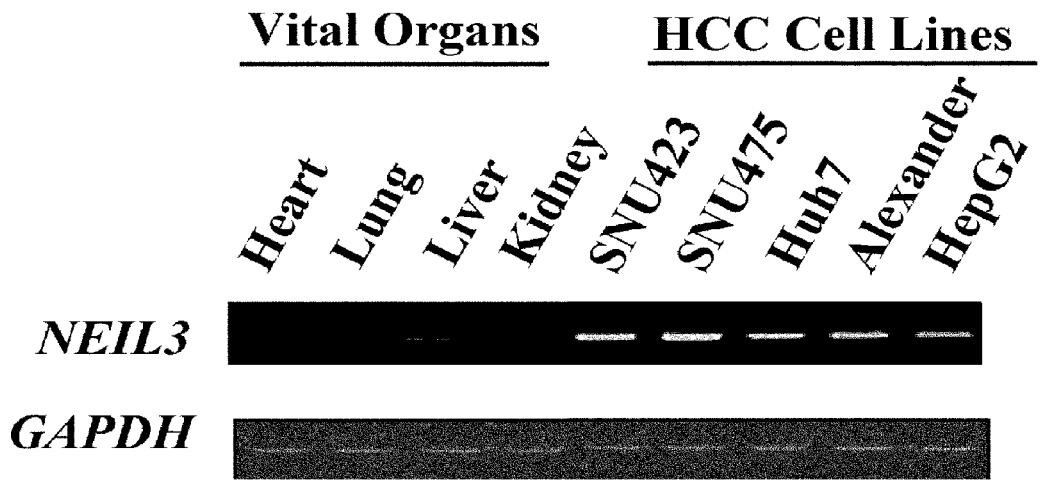

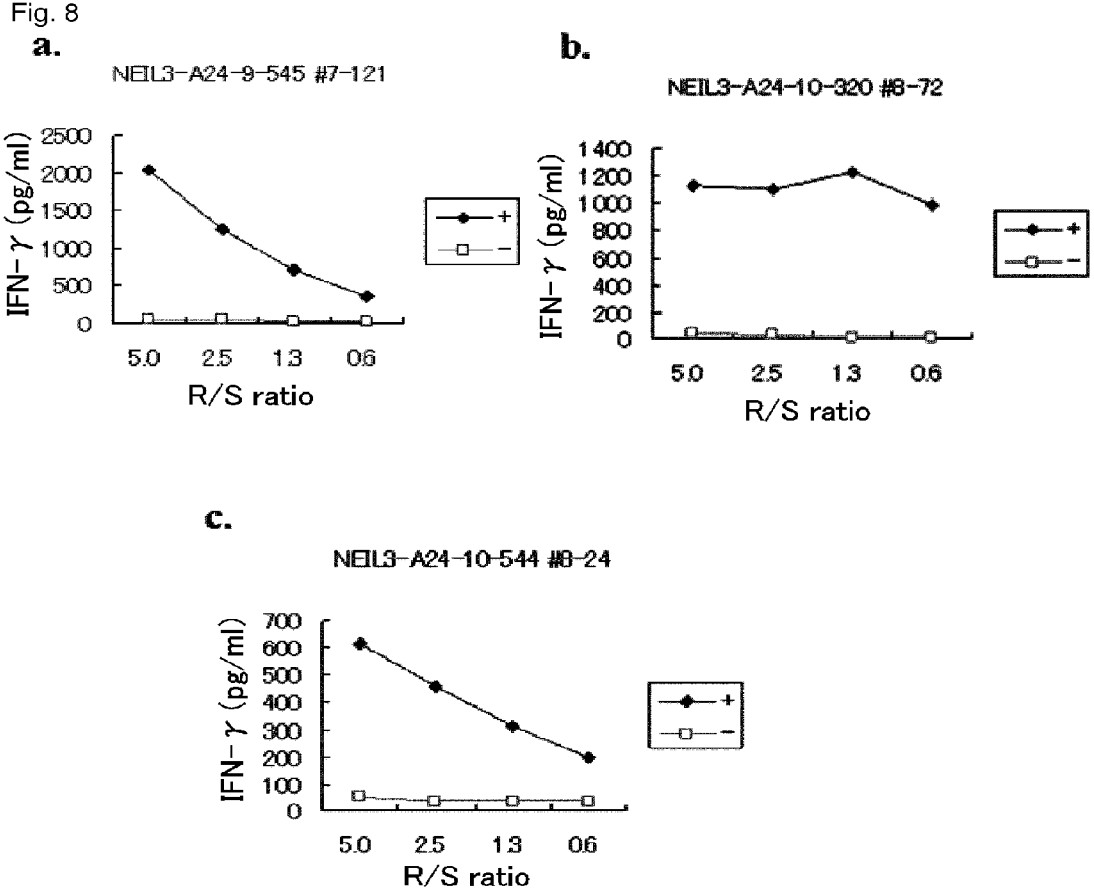
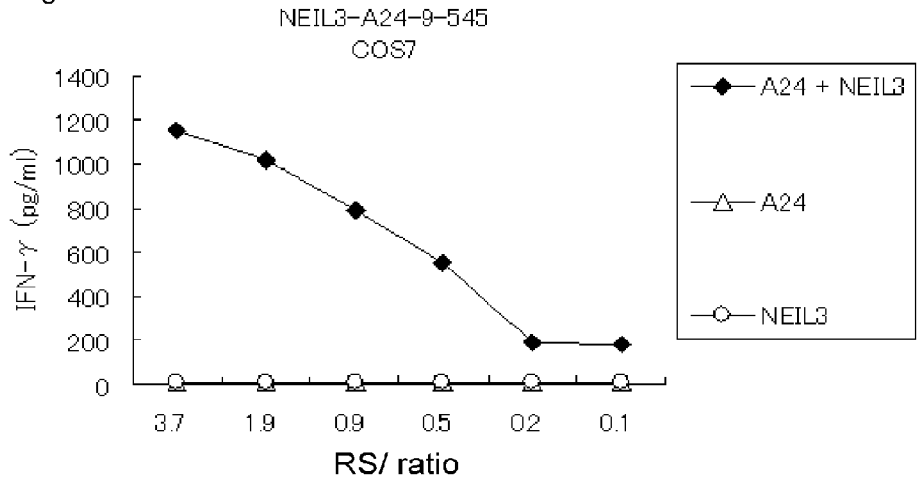

NEIL3 PEPTIDES AND VACCINES INCLUDING THE SAME

TECHNICAL FIELD

The present application is a U.S. National Stage Application of PCT/JP2010/001808, filed Mar. 15, 2010, which claims the benefit of U.S. Provisional Applications No. 61/210,512, filed on Mar. 18, 2009, the entire contents of which are incorporated by reference herein in their entirety.

The present invention relates to the field of biological science, more specifically to the field of cancer therapy. In particular, the present invention relates to novel peptides that are extremely effective as cancer vaccines, and drugs for treating and preventing tumors.

BACKGROUND ART

It has been demonstrated that CD8 positive CTLs recognize epitope peptides derived from tumor-associated antigens (TAAs) on major histocompatibility complex (MHC) class I molecule, and then kill the tumor cells. Since the discovery of melanoma antigen (MAGE) family as the first example of TAAs, many other TAAs have been discovered through immunological approaches (NPL 1/Boon T, Int J Cancer 1993 May 8, 54(2): 177-80; NPL 2/Boon T & van der Bruggen P, J Exp Med 1996 Mar. 1, 183(3): 725-9), and some of the TAAs are now in the process of clinical development as immunotherapeutic targets.

Identification of new TAAs, which induce potent and specific anti-tumor immune responses, warrants further development of clinical application of peptide vaccination strategy in various types of cancer (NPL 3/Harris CC, J Natl Cancer Inst 1996 Oct. 16, 88(20): 1442-55; NPL 4/Butterfield L H et al., Cancer Res 1999 Jul. 1, 59(13): 3134-42; NPL 5/Vissers J L et al., Cancer Res 1999 Nov. 1, 59(21): 5554-9; NPL 6/van der Burg S H et al., J Immunol 1996 May 1, 156(9): 3308-14; NPL 7/Tanaka F et al., Cancer Res 1997 Oct. 15, 57(20): 4465-8; NPL 8/Fujie T et al., Int J Cancer 1999 Jan. 18, 80(2): 169-72; NPL 9/Kikuchi M et al., Int J Cancer 1999 May 5, 81(3): 459-66; NPL 10/Oiso M et al., Int J Cancer 1999 May 5, 81(3): 387-94). Until now, several clinical trials using these tumor-associated antigen derived peptides have been reported. Unfortunately, only a low objective response rate could be observed in these cancer vaccine trials so far (NPL 11/Belli F et al., J Clin Oncol 2002 Oct. 15, 20(20): 4169-80; NPL 12/Coulie P G et al., Immunol Rev 2002 October, 188: 33-42; NPL 13/Rosenberg S A et al., Nat Med 2004 September, 10(9): 909-15).

Favorable TAA is indispensable for proliferation and survival of cancer cells, as a target for immunotherapy, because the use of such TAAs may minimize the well-described risk of immune escape of cancer cells attributable to deletion, mutation, or down-regulation of TAAs as a consequence of therapeutically driven immune selection.

On the other hand, Nei endonuclease VIII-like 3 (NEIL3) has been isolated as a member belonging to a class of DNA glycosylases homologous to the bacterial Fpg/Nei family (NPL 14/Bandaru et al., DNA Repair (Amst). 2002 Jul. 17; 1(7):517-29). These glycosylases initiate the first step in base excision repair by cleaving bases damaged by reactive oxygen species and introducing a DNA strand break via the associated lyase reaction. NEIL3 is likely to play a role in DNA repair mechanism, however, its relationship with carcinogenesis has not been elucidated.

CITATION LIST

Non Patent Literature

[NPL 1] Boon T, Int J Cancer 1993 May 8, 54(2): 177-80

[NPL 2] Boon T & van der Bruggen P, J Exp Med 1996 Mar. 1, 183(3): 725-9

[NPL 3] Harris C C, J Natl Cancer Inst 1996 Oct. 16, 88(20): 1442-55

[NPL 4] Butterfield L H et al., Cancer Res 1999 Jul. 1, 59(13): 3134-42

[NPL 5] Vissers J L et al., Cancer Res 1999 Nov. 1, 59(21): 5554-9

[NPL 6] van der Burg S H et al., J Immunol 1996 May 1, 156(9): 3308-14

[NPL 7] Tanaka F et al., Cancer Res 1997 Oct. 15, 57(20): 4465-8

[NPL 8] Fujie T et al., Int J Cancer 1999 Jan. 18, 80(2): 169-72

[NPL 9] Kikuchi M et al., Int J Cancer 1999 May 5, 81(3): 459-66

[NPL 10] Oiso M et al., Int J Cancer 1999 May 5, 81(3): 387-94

[NPL 11] Belli F et al., J Clin Oncol 2002 Oct. 15, 20(20): 4169-80

[NPL 12] Coulie P G et al., Immunol Rev 2002 October, 188: 33-42

[NPL 13] Rosenberg S A et al., Nat Med 2004 September, 10(9): 909-15

[NPL 14] Bandaru et al., DNA Repair (Amst). 2002 Jul. 17; 1(7):517-29

SUMMARY OF INVENTION

The present invention is based, at least in part, on the discovery of the applicable targets of immunotherapy. Because TAAs are generally perceived by the immune system as "self" and therefore often have no immunogenicity, the discovery of appropriate targets is of extreme importance. As noted above, NEIL3 (SEQ ID NO: 45 encoded by the gene of GenBank Accession No. NM_018248 (for example, SEQ ID NO: 44)) has been identified as up-regulated in cancers, such as bladder cancer, breast cancer, cervical cancer, cholangiocellular carcinoma, colorectal cancer, endometriosis, esophagus cancer, liver cancer, non-small cell lung cancer (NSCLC), osteosarcoma, pancreatic cancer, prostate cancer, renal carcinoma, small cell lung cancer (SCLC), soft tissue tumor, acute myeloid leukemia (AML) and chronic myeloid leukemia (CML). Thus, NEIL3 is a candidate for the target of cancer/tumor immunotherapy.

The present invention is based, at least in part, on the identification of specific epitope peptides of the gene products of NEIL3 which possess the ability to induce CTLs specific to NEIL3. As discussed in detail below, peripheral blood mononuclear cells (PBMCs) obtained from a healthy donor were stimulated using HLA-A*2402 or HLA-A*0201 binding candidate peptides derived from NEIL3. CTL lines were then established with specific cytotoxicity against the HLA-A24 or HLA-A2 positive target cells pulsed with each of candidate peptides. These results demonstrate that these peptides are HLA-A24 or HLA-A2 restricted epitope peptides that may induce potent and specific immune responses against cells expressing NEIL3. Further, it indicated that NEIL3 is strongly immunogenic and the epitopes thereof are effective targets for cancer/tumor immunotherapy.

Accordingly, the present invention provides isolated peptides binding to HLA antigen which consists of NEIL3 (SEQ ID NO: 45) or the immunologically active fragments thereof. These peptides are expected to have CTL inducibility and can be used to induce CTL ex vivo or to be administered to a subject for inducing immune responses against cancers such as bladder cancer, breast cancer, cervical cancer, cholangiocellular carcinoma, endometriosis, liver cancer, NSCLC, osteosarcoma, pancreatic cancer, SCLC and AML. Preferably, those peptides are nonapeptide or decapeptide, and more preferably, consisting of the amino acid sequence selected from the group consisting of SEQ ID NOs: 1 to 43. In particular, the peptides consisting of the amino sequence selected from the group consisting of SEQ ID NOs: 3, 4, 5, 6, 11, 15, 17, 21, 22, 24, 33, 35, 41 and 43 showed strong CTL inducibility.

The peptides of the present invention encompass those wherein one, two or more amino acids are substituted deleted or added, so long as the modified peptides retain the original CTL inducibility.

Further, the present invention provides isolated polynucleotides encoding any peptides of the present invention. These polynucleotides can be used for inducing or preparing APCs with CTL inducibility or to be administered to a subject for inducing immune responses against cancers as well as the present peptides.

When administered to a subject, the present peptides are presented on the surface of APCs and then induce CTLs targeting the respective peptides. Therefore, according to an aspect of the present invention, compositions or substances including any peptides or polynucleotides of the present invention for inducing CTLs are also provided. Furthermore, compositions or substances including any peptides or polynucleotides can be used to treating and/or prophylaxis of cancers, such as bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML, and/or preventing postoperative recurrence thereof. Thus, the present invention also provides pharmaceutical compositions or substances for treating and/or prophylaxis of cancers, and/or preventing postoperative recurrence thereof, which includes any peptides or polynucleotides of the present invention. The present pharmaceutical compositions or substances may include APCs or exosomes which present any of the present peptides instead of/in addition to the present peptides or polynucleotides as active ingredients.

The peptides or polynucleotides of the present invention can induce APCs which present on their surface a complex of an HLA antigen and the present peptide, for example, by contacting APCs derived from a subject with the peptide or introducing a polynucleotide encoding a peptide of the present invention into APCs. Such APCs have high CTL inducibility against target peptides and find use in cancer immunotherapy. Therefore, the present invention encompasses the methods for inducing APCs with CTL inducibility and the APCs obtained by the methods.

The present invention also provides a method for inducing CTL, which includes the step of co-culturing CD8 positive cells with APCs or exosomes presenting the peptide of the present invention on its surface or the step of introducing a gene that includes a polynucleotide encoding a T cell receptor (TCR) subunit polypeptide binding to the present peptide. The CTLs obtained by the methods can find use for treating and/or preventing cancers, such as bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML. Therefore, the present invention encompasses the CTLs obtained by the present methods.

Moreover, the present invention provides methods for inducing immune response against cancers, which methods include the step of administering compositions or substances including the NEIL3 polypeptides or immunologically active fragments thereof, polynucleotides encoding NEIL3 polypeptides, exosomes or the APCs presenting NEIL3 polypeptides.

The present invention also provides a method of diagnosing cancer, including, but not limited to, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

The present invention may be applied to any diseases relating to NEIL3 overexpression, such as cancer, exemplary cancers include bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

BRIEF DESCRIPTION OF DRAWINGS

FIG. 1 depicts photographs showing the results of IFN-gamma ELISPOT assay on CTLs that were induced with peptides derived from NEIL3. The CTLs in the well number #8 stimulated with NEIL3-A2-9-585 (SEQ ID NO: 3) (a), #2 with NEIL3-A2-9-127 (SEQ ID NO: 4) (b), #4 and 5 with NEIL3-A2-9-416 (SEQ ID NO: 5) (c), #3 with NEIL3-A2-9-71 (SEQ ID NO: 6) (d), #1 with NEIL3-A2-9-271 (SEQ ID NO: 11) (e), #3 with NEIL3-A2-10-198 (SEQ ID NO: 15) (f), #1 with NEIL3-A2-10-340 (SEQ ID NO: 17) (g), #2 and 3 with NEIL3-A2-10-590 (SEQ ID NO: 21) (h), #6 with NEIL3-A2-10-378 (SEQ ID NO: 22) (i) and #9, 10, 12 and 13 with NEIL3-A2-9-416 (SEQ ID NO: 5) (for HLA-A0206) (j) showed potent IFN-gamma production compared with the control, respectively. The square on the well of these pictures indicates that the cells from corresponding well were expanded to establish CTL lines. In the figures, "+" indicates the IFN-gamma production against target cells pulsed with the appropriate peptide, and "−" indicates the IFN-gamma production against target cells not pulsed with any peptides.

[FIG. 2-1] FIG. 2-1 depicts line graphs showing the IFN-gamma production of CTL lines stimulated with NEIL3-A2-585 (SEQ ID NO: 3) (a), NEIL3-A2-9-127 (SEQ ID NO: 4) (b), NEIL3-A2-9-416 (SEQ ID NO: 5) (c)(d), and NEIL3-A2-9-71 (SEQ ID NO: 6) (e) detected by IFN-gamma ELISA assay. It demonstrated that CTL lines established by stimulation with each peptide showed potent IFN-gamma production compared with the control. In the figures, "+" indicates the IFN-gamma production against target cells pulsed with the appropriate peptide and "−" indicates the IFN-gamma production against target cells not pulsed with any peptides.

[FIG. 2-2] FIG. 2-2 depicts line graphs showing the IFN-gamma production of CTL lines stimulated with NEIL3-A2-9-271 (SEQ ID NO: 11) (f), NEIL3-A2-10-198 (SEQ ID NO: 15) (g), NEIL3-A2-10-590 (SEQ ID NO: 21) (h)(i) and NEIL3-A2-9-416 (SEQ ID NO: 5) (for HLA-A0206) (j)(k) detected by IFN-gamma ELISA assay. It demonstrated that CTL lines established by stimulation with each peptide showed potent IFN-gamma production compared with the control. In the figures, "+" indicates the IFN-gamma production against target cells pulsed with the appropriate peptide and "−" indicates the IFN-gamma production against target cells not pulsed with any peptides.

FIG. 3 shows the IFN-gamma production of the CTL clones established by limiting dilution from the CTL lines stimulated with NEIL3-A2-9-416 (SEQ ID NO: 5) (a), NEIL3-A2-9-71 (SEQ ID NO: 6) (b), NEIL3-A2-10-198 (SEQ ID NO: 15) (c), NEIL3-A2-10-590 (SEQ ID NO: 21) (d) and NEIL3-A2-9-416 (SEQ ID NO: 5) (e) (for HLA-A0206). It demonstrated that the CTL clones established by stimulation with NEIL3-A2-9-416 (SEQ ID NO: 5) (a), NEIL3-A2-9-71 (SEQ ID NO: 6) (b), NEIL3-A2-10-198 (SEQ ID NO: 15) (c), NEIL3-A2-10-590 (SEQ ID NO: 21) (d) and NEIL3-A2-9-416 (SEQ ID NO: 5) (e) (for HLA-A0206) showed potent IFN-gamma production compared with the control. In the figure, "+" indicates the IFN-gamma production against target cells pulsed with NEIL3-A2-9-416 (SEQ ID NO: 5) (a), NEIL3-A2-9-71 (SEQ ID NO: 6) (b), NEIL3-A2-10-198 (SEQ ID NO: 15) (c), NEIL3-A2-10-590 (SEQ ID NO: 21) (d) and NEIL3-A2-9-416 (SEQ ID NO: 5) (for HLA-A0206) (e), and "−" indicates the IFN-gamma production against target cells not pulsed with any peptides.

[FIG. 4-1]FIG. 4-1 depicts line graphs showing specific CTL activity against the target cells that exogenously express NEIL3 and HLA-A*0201 or HLA-A*0206. COS7 cells transfected with HLA-A*0201, with HLA-A*0206 or with the full length NEIL3 gene were prepared as control. The CTL clones established with NEIL3-A2-9-416 (SEQ ID NO: 5) (a), NEIL3-A2-9-71 (SEQ ID NO: 6) (b), and NEIL3-A2-10-198 (SEQ ID NO: 15) (c) showed specific CTL activity against COS7 cells transfected with both NEIL3 and HLA-A*0201 (black lozenge). On the other hand, no significant specific CTL activity was detected against target cells expressing either HLA (triangle) or NEIL3 (circle).

[FIG. 4-2]FIG. 4-2 depicts line graphs showing specific CTL activity against the target cells that exogenously express NEIL3 and HLA-A*0201 or HLA-A*0206. COS7 cells transfected with HLA-A*0201, with HLA-A*0206 or with the full length NEIL3 gene were prepared as control. The CTL clones established with NEIL3-A2-9-416 (SEQ ID NO: 5) (d) (for HLA-A0206) showed specific CTL activity against COS7 cells transfected with both NEIL3 and HLA-A*0206 (black lozenge). On the other hand, no significant specific CTL activity was detected against target cells expressing either HLA (triangle) or NEIL3 (circle).

[FIG. 5]FIG. 5 depicts photographs showing the expression of NEIL3 in liver cancer. Part A shows expression of NEIL3 in clinical liver cancer tissues examined by semi-quantitative RT-PCR. Part B shoes expression of NEIL3 in HCC cell lines examined by semiquantitative RT-PCR.

FIG. 6 depicts photographs showing the results of IFN-gamma ELISPOT assay on CTLs that were induced with peptides derived from NEIL3. The CTLs in the well number #7 stimulated with NEIL3-A24-9-545 (SEQ ID NO: 24) (a), #6 with NEIL3-A24-9-362 (SEQ ID NO: 33) (b), #2 and #8 with NEIL3-A24-10-320 (SEQ ID NO: 35) (c), #8 with NEIL3-A24-10-544 (SEQ ID NO: 41) (d), #1 and #4 with NEIL3-A24-10-87 (SEQ ID NO: 43) (e) showed potent IFN-gamma production compared with the control, respectively. The square on the well of these pictures indicates that the cells from corresponding well were expanded to establish CTL line. In contrast, as typical case of negative data, it was not shown specific IFN-gamma production from the CTL stimulated with NEIL3-A24-9-364 (SEQ ID NO: 25) (f) against peptide-pulsed target cells. In the figures, "+" indicates the IFN-gamma production against target cells pulsed with the appropriate peptide, and "−" indicates the IFN-gamma production against target cells not pulsed with any peptides.

FIG. 7 depicts line graphs showing the IFN-gamma production of the CTL lines stimulated with NEIL3-A24-9-545 (SEQ ID NO: 24) (a), NEIL3-A24-9-362 (SEQ ID NO: 33) (b), NEIL3-A24-10-320 (SEQ ID NO: 35) (c), NEIL3-A24-10-544 (SEQ ID NO: 41) (d) and NEIL3-A24-10-87 (SEQ ID NO: 43) (e) detected by IFN-gamma ELISA assay. It demonstrated that CTL lines established by stimulation with each peptide showed potent IFN-gamma production compared with the control. In the figures, "+" indicates the IFN-gamma production against target cells pulsed with the appropriate peptide, and "−" indicates the IFN-gamma production against target cells not pulsed with any peptides.

[FIG. 8]FIG. 8 depicts line graphs shows the IFN-gamma production of the CTL clones established by limiting dilution from the CTL lines stimulated with NEIL3-A24-9-545 (SEQ ID NO: 24) (a), NEIL3-A24-10-320 (SEQ ID NO: 35) (b) and NEIL3-A24-10-544 (SEQ ID NO: 41) (c). It demonstrated that the CTL clones established by stimulation with each peptide showed potent IFN-gamma production compared with the control. In the figure, "+" indicates the IFN-gamma production against target cells pulsed with the appropriate peptide and "−" indicates the IFN-gamma production against target cells not pulsed with any peptides.

[FIG. 9]FIG. 9 depicts line graph showing specific CTL activity against the target cells that exogenously express NEIL3 and HLA-A*2402. COS7 cells transfected with HLA-A*2402 or the full length of NEIL3 gene were prepared as controls. The CTL clone established with NEIL3-A24-9-545 (SEQ ID NO: 24) showed specific CTL activity against COS7 cells transfected with both NEIL3 and HLA-A*2402 (black lozenge). On the other hand, no significant specific CTL activity was detected against target cells expressing either HLA-A*2402 (triangle) or NEIL3 (circle).

DESCRIPTION OF EMBODIMENTS

Figure 1:
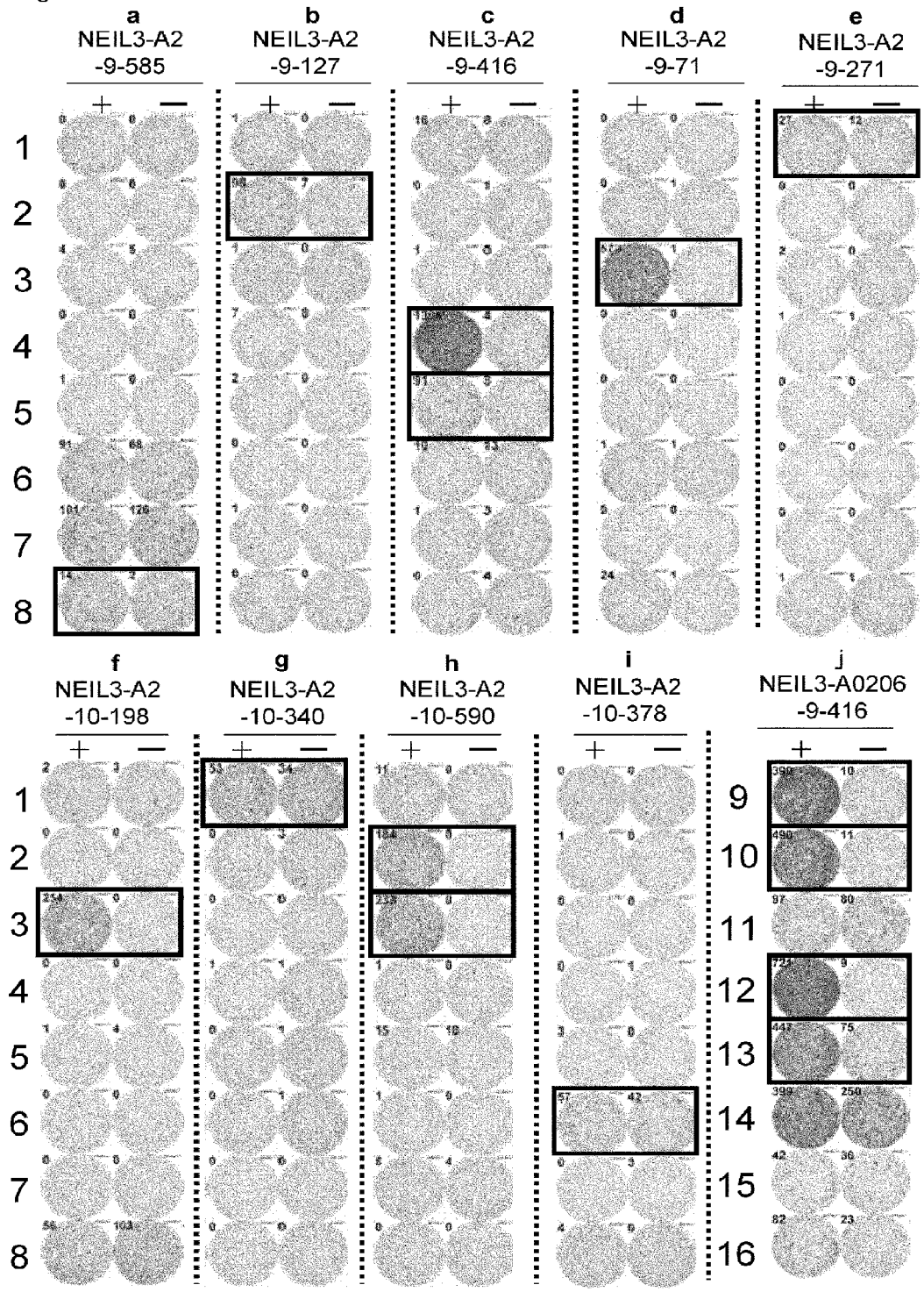
[FIG. 1]
Figures 1, 2:
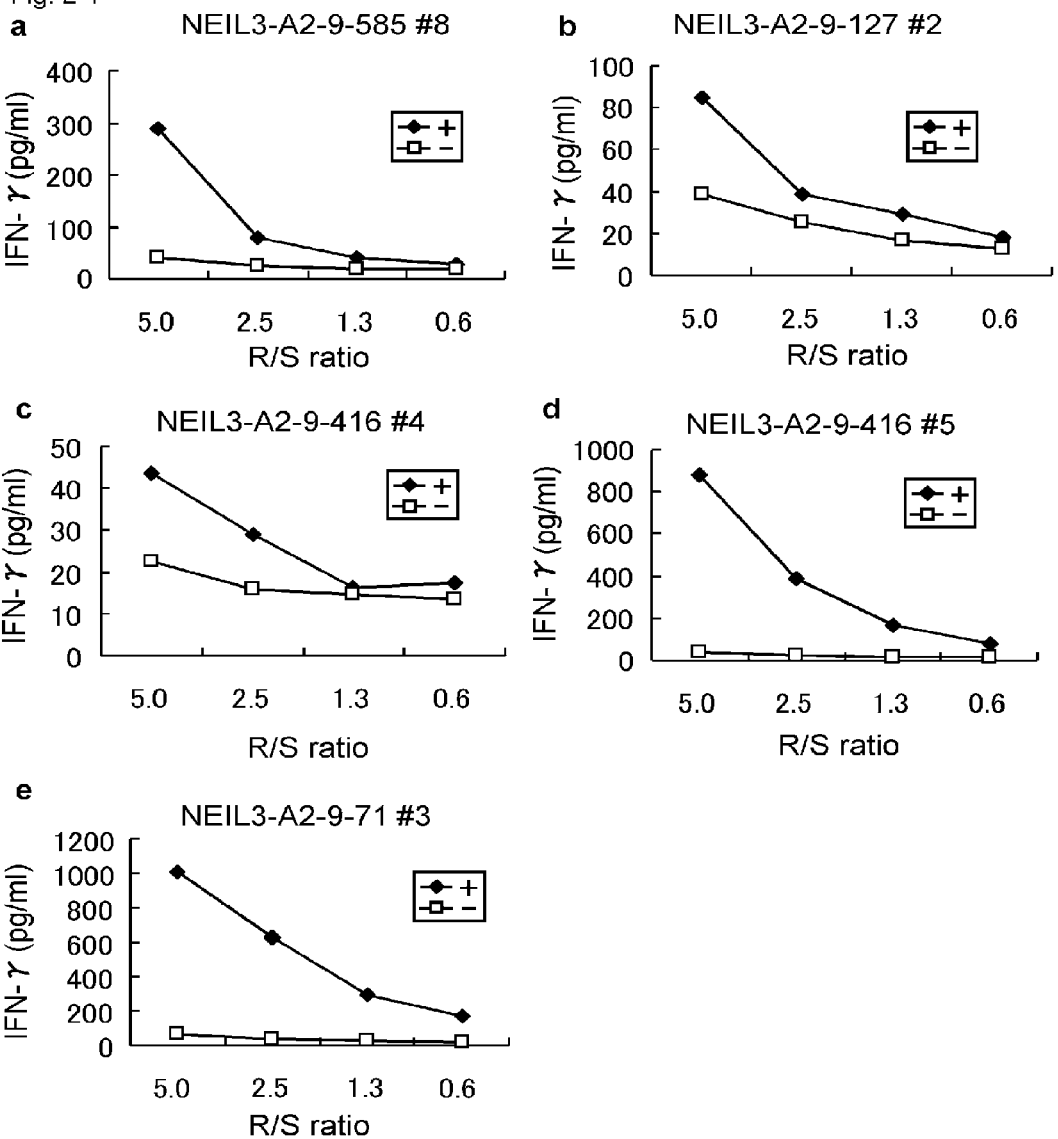

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and/or optimization. It is also to be understood that the terminology used in the description is for the purpose of describing the particular versions or embodiments only, and is not intended to limit the scope of the present invention which will be limited only by the appended claims.

I. Definitions

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are similarly to the amino acids referred to by their commonly accepted single-letter codes.

Unless otherwise defined, the term "cancer" refers to the cancers overexpressing NEIL3 gene, examples of which include, but are not limited to, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the terms "HLA-A24" refers to the HLA-A24 type containing the subtypes such as HLA-A*2402.

Unless otherwise defined, the term "HLA-A2", as used herein, representatively refers to the subtypes such as HLA-A*0201 and HLA-A*0206.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

Unless otherwise defined, all technical and scientific terms used herein have the same meaning as commonly understood by one of ordinary skill in the art to which the present invention belongs.

II. Peptides

To demonstrate that peptides derived from NEIL3 function as an antigen recognized by CTLs, peptides derived from NEIL3 (SEQ ID NO: 45) were analyzed to determine whether they were antigen epitopes restricted by HLA-A24 or A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A2 binding peptides derived from NEIL3 were identified using the information on their binding affinities to HLA-A2. The candidate peptide is the peptides selected from the group consisting of SEQ ID NOs: 1 to 23.

Moreover, after in vitro stimulation of T-cells by dendritic cells (DCs) pulsed (loaded) with these peptides, CTLs were successfully established using each of the following peptides;
NEIL3-A2-9-585 (SEQ ID NO: 3),
NEIL3-A2-9-127 (SEQ ID NO: 4),
NEIL3-A2-9-416 (SEQ ID NO: 5),
NEIL3-A2-9-71 (SEQ ID NO: 6),
NEIL3-A2-9-271 (SEQ ID NO: 11),
NEIL3-A2-10-198 (SEQ ID NO: 15),
NEIL3-A2-10-340 (SEQ ID NO: 17),
NEIL3-A2-10-590 (SEQ ID NO: 21), and
NEIL3-A2-10-378 (SEQ ID NO: 22).

Candidates of HLA-A24 binding peptides derived from NEIL3 were identified based on their binding affinities to HLA-A24. The candidate peptide is the peptides selected from the group consisting of SEQ ID NOs: 24 to 43.

Moreover, after in vitro stimulation of T-cells by dendritic cells (DCs) pulsed (loaded) with these peptides, CTLs were successfully established using each of the following peptides;
NEIL3-A24-9-545 (SEQ ID NO: 24),
NEIL3-A24-9-362 (SEQ ID NO: 33),
NEIL3-A24-10-320 (SEQ ID NO: 35),
NEIL3-A24-10-544 (SEQ ID NO: 41), and
NEIL3-A24-10-87 (SEQ ID NO: 43). These established CTLs showed potent specific CTL activity against target cells pulsed with respective peptides. These results demonstrate that NEIL3 is an antigen recognized by CTLs and that the peptides tested are epitope peptides of NEIL3 restricted by HLA-A24 or HLA-A2.

Since the NEIL3 gene is overexpressed in cancer cells such as bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML and not expressed in most normal organs, it is a good target for cancer immunotherapy. Thus, the present invention provides nonapeptides (peptides consisting of nine amino acid residues) and decapeptides (peptides consisting of ten amino acid residues) of CTL-recognized epitopes from NEIL3. Alternatively, the present invention provides isolated peptides which bind to HLA antigens and induce cytotoxic T lymphocytes (CTLs), wherein the peptide consists of the amino acid sequence of SEQ ID NO: 45 or is an immunologically active fragment thereof. More specifically, in some embodiments, the present invention provides peptides consisting of the amino acid sequence selected from the group consisting of SEQ ID NOs: 3, 4, 5, 6, 11, 15, 17, 21, 22, 24, 33, 35, 41 and 43.

Generally, software programs now available, for example, on the Internet, such as those described in Parker K C et al., J Immunol 1994 Jan. 1, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994 Jan. 1, 152(1): 163-75, Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. The methods for determining binding affinity is described, for example, in; Journal of Immunological Methods, 1995, 185: 181-190; Protein Science, 2000, 9: 1838-1846. Therefore, one can select fragments derived from NEIL3, which have high binding affinity with HLA antigens using such software programs. Thus, the present invention encompasses peptides consisting of any fragments derived from NEIL3, which would be determined to bind with HLA antigens by such known programs. Furthermore, such peptides may include the peptide consisting of the full length of NEIL3.

The peptides of the present invention may be flanked with additional amino acid residues so long as the peptides retain their CTL inducibility. The additional amino acid residues may be composed of any kind of amino acids so long as they do not impair the CTL inducibility of the original peptide. Thus, the present invention encompasses peptides with binding affinity to HLA antigens, including peptides derived from NEIL3. Such peptides are, for example, less than about 40 amino acids, often less than about 20 amino acids, usually less than about 15 amino acids.

Generally, it is known that modifications of one or more amino acids in a peptide do not influence the function of the peptide, or in some cases even enhance the desired function of the original protein. In fact, modified peptides (i.e., peptides composed of an amino acid sequence modified by substituting deleting or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, according to one embodiment of the present invention, the peptide having CTL inducibility of the present invention may be composed of the peptide consisting of the amino acid sequence selected from the group consisting of SEQ ID NOs: 3, 4, 5, 6, 11, 15, 17, 21, 22, 24, 33, 35, 41 and 43, wherein one, two or even more amino acids are added, deleted and/or substituted.

One of skill in the art will recognize that individual additions deletions or substitutions to an amino acid sequence which alters a single amino acid or a small percentage of amino acids results in the conservation of the properties of the original amino acid side-chain; it is thus referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic group containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, the peptide of the present invention is not restricted thereto and may include non-conservative modifications, so long as the peptide retains the CTL inducibility. Furthermore, the modified peptides do not exclude CTL inducible peptides of polymorphic variants, interspecies homologues, and alleles of NEIL3.

To retain the requisite CTL inducibility one can modify (add or substitute) a small number (for example, 1, 2 or several) or a small percentage of amino acids. Herein, the term "several" means 5 or fewer amino acids, for example, 3 or fewer. The percentage of amino acids to be modified may be 20% or less, for example, 15% of less, for example 10% or 1 to 5%.

Moreover, the peptides may be substituted or added by such of the amino acid residues to achieve a higher binding affinity. When used in cancer immunotherapy, the present peptides are presented on the surface of a cell or exosome as a complex with an HLA antigen. In addition to peptides that are naturally displayed, since the regularity of the sequences of peptides displayed by binding to HLA antigens has already been known (J Immunol 1994, 152: 3913; Immunogenetics 1995, 41: 178; J Immunol 1994, 155: 4307), modifications based on such regularity may be introduced into the immunogenic peptides of the present invention.

For example, peptides showing high HLA-A2 binding affinity have their second amino acid from the N-terminus substituted with leucine or methionine, and peptides whose amino acid at the C-terminus is substituted with valine or leucine can also be favorably used. Thus, peptides having the amino acid sequences selected from the group consisting of SEQ ID NOs: 3, 4, 5, 6, 11, 15, 17, 21 and 22 wherein the second amino acid from the N-terminus of the amino acid sequence of the SEQ ID NO is substituted with leucine or methionine, and peptides, and/or wherein the C-terminus of the amino acid sequence of the SEQ ID NO is substituted with valine or leucine are encompassed by the present invention.

On the other hand, peptides possessing high HLA-A24 binding affinity have their second amino acid from the N-terminus substituted with phenylalanine, tyrosine, methionine, or tryptophan, and the amino acid at the C-terminus is substituted with phenylalanine, leucine, isoleucine, tryptophan, or methionine. Thus, peptides having the amino acid sequences of SEQ ID NOs: 24, 33, 35, 41 and 43 wherein the second amino acid from the N-terminus is substituted with phenylalanine, tyrosine, methionine, or tryptophan, and/or wherein the C-terminus is substituted with phenylalanine, leucine, isoleucine, tryptophan, or methionine are encompassed by the present invention.

Substitutions may be introduced not only at the terminal amino acids but also at the position of potential T cell receptor (TCR) recognition of peptides. Several studies have demonstrated that a peptide with amino acid substitutions may have equal to or better function than that of the original, for example, CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002) February 1; 168(3):1338-47., S. O. Dionne et al. Cancer Immunol immunother. (2003) 52: 199-206 and S. O. Dionne et al. Cancer Immunology, Immunotherapy (2004) 53, 307-314).

Furthermore, one, two or several amino acids may also be added to the N and/or C-terminus of the present peptides. Such modified peptides with high HLA antigen binding affinity and retained CTL inducibility are also included in the present invention.

However, when the peptide sequence is identical to a portion of the amino acid sequence of an endogenous or exogenous protein having a different function, side effects such as autoimmune disorders or allergic symptoms against specific substances may be induced. Therefore, one can perform homology searches using available databases to avoid situations in which the sequence of the peptide matches the amino acid sequence of another protein. When it becomes clear from the homology searches that there exists not even a peptide with 1 or 2 amino acids difference to the objective peptide, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8 positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependent on MHC (HLA) class II restricted T(H) response) can be used. For example, the target cells may be radiolabeled with $^{51}$Cr and such, and cytotoxic activity may be calculated from radioactivity released from the target cells. Alternatively, it may be examined by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, nonapeptides or decapeptides selected from peptides consisting of the amino acid sequences indicated by SEQ ID NOs: 3, 4, 5, 6, 11, 15, 17, 21, 22, 24, 33, 35, 41 and 43 showed particularly high CTL inducibility as well as high binding affinity to an HLA antigen. Thus, these peptides are exemplified embodiments of the present invention.

Furthermore, the result of homology analysis showed that those peptides do not have significant homology with peptides derived from any other known human gene products. This lowers the possibility of unknown or undesired immune responses when used for immunotherapy. Therefore, also from this aspect, these peptides find use for eliciting immunity in cancer patients against NEIL3. Thus, the peptides of the present invention, preferably, peptides consisting of the amino acid sequence selected from the group consisting of SEQ ID NOs: 3, 4, 5, 6, 11, 15, 17, 21, 22, 24, 33, 35, 41 and 43.

In addition to modification of the present peptides, discussed above, the peptides of the present invention may be linked to other peptides, so long as they retain the CTL inducibility. Exemplified other peptides include: the peptides of the present invention or the CTL inducible peptides derived from other TAAs. The linkers between the peptides are well known in the art, for example, AAY (P. M. Daftarian et al., J Trans Med 2007, 5:26), AAA, NKRK (R. P. M. Sutmuller et al., J. Immunol. 2000, 165: 7308-7315) or K (S. Ota et al., Can Res. 62, 1471-1476, K. S. Kawamura et al., J. Immunol. 2002, 168: 5709-5715).

For example, non-NEIL3 tumor associated antigen peptides also can be used substantially simultaneously to increase immune response via HLA class I and/or class II. It is well established that cancer cells can express more than one tumor associated gene. It is within the scope of routine experimentation for one of ordinary skill in the art to determine whether a particular subject expresses additional tumor associated genes, and then to include HLA class I and/or HLA class II binding peptides derived from expression products of such genes in NEIL3 compositions or vaccines according to the present invention.

Examples of HLA class I and HLA class II binding peptides will be known to one of ordinary skill in the art (for example, see Coulie, Stem Cells 13:393-403, 1995), and can be used in the invention in a like manner as those disclosed herein. One of ordinary skill in the art can prepare polypeptides including one or more NEIL3 peptides and one or more of the non-NEIL3 peptides, or nucleic acids encoding such polypeptides, according to standard procedures of molecular biology.

Thus, such "polytopes" are groups of two or more potentially immunogenic or immune response stimulating peptides which can be joined together in various arrangements (e.g., concatenated, overlapping). The polytope (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J. Immunol. 157(2):822-826, 1996; Tarn et al., J. Exp. Med. 171(1):299-306, 1990). Polytopes containing various numbers and combinations of epitopes can be prepared and tested for recognition by CTLs and for efficacy in increasing an immune response.

Furthermore, the peptides of the present invention may be further linked to other substances, so long as they retain the CTL inducibility. Such substances may include: peptides, lipids, sugar and sugar chains, acetyl groups, natural and synthetic polymers, etc. The peptides may contain modifications such as glycosylation, side chain oxidation, or phosphorylation; so long as the modifications do not destroy the biological activity of the peptides as described herein. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adopted for the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted or added by one, two or several amino acid residues, those having same or higher activity as compared to original peptides can be screened for or selected. The present invention, therefore, also provides the method of screening for or selecting modified peptides having same or higher activity as compared to originals. For example, the method may include steps of:

a: substituting, deleting or adding at least one amino acid residue of a peptide of the present invention, b: determining the activity of the peptide, and c: selecting the peptide having same or higher activity as compared to the original.

Herein, the activity may include MHC binding activity, APC or CTL inducibility and cytotoxic activity.

Herein, the peptides of the present invention may also be described as "NEIL3 peptide(s)" or "NEIL3 polypeptide(s)".

III. Preparation of NEIL3 Peptides

The peptides of the present invention may be prepared using well known techniques. For example, the peptides may be prepared synthetically, by recombinant DNA technology or chemical synthesis. The peptides of the present invention may be synthesized individually or as longer polypeptides including two or more peptides. The peptides may be isolated, i.e., purified or isolated substantially free from other naturally occurring host cell proteins and fragments thereof, or any other chemical substances.

The peptides of the present invention may contain modifications, such as glycosylation, side chain oxidation, or phosphorylation; so long as the modifications do not destroy the biological activity of the peptides as described herein. Other modifications include incorporation of D-amino acids or other amino acid mimetics that may be used, for example, to increase the serum half life of the peptides.

A peptide of the present invention may be obtained through chemical synthesis based on the selected amino acid sequence. For example, conventional peptide synthesis methods that may be adopted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides may be obtained adopting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. Polynucleotides

The present invention provides polynucleotides which encode any of the aforementioned peptides of the present invention. These include polynucleotides derived from the natural occurring NEIL3 gene (GenBank Accession No. NM_018248 (for example, SEQ ID NO: 44)) and those having a conservatively modified nucleotide sequences thereof. Herein, the phrase "conservatively modified nucleotide sequence" refers to sequences which encode identical or essentially identical amino acid sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of skill in the art will recognize that each codon in a nucleic acid (except AUG, which is ordinarily the only codon for methionine, and TGG, which is ordinarily the only codon for tryptophan) may be modified to yield a functionally identical molecule. Accordingly, each silent variation of a nucleic acid that encodes a peptide is implicitly described in each disclosed sequence.

The polynucleotide of the present invention may be composed of DNA, RNA, or derivatives thereof. As is well known in the art, a DNA molecule is composed of bases such as the naturally occurring bases A, T, C, and G, and T is replaced by U in an RNA. One of skill will recognize that non-naturally occurring bases be included in polynucleotides, as well.

The polynucleotide of the present invention may encode multiple peptides of the present invention with or without intervening amino acid sequences. For example, the intervening amino acid sequence may provide a cleavage site (e.g., enzyme recognition sequence) of the polynucleotide or the translated peptides. Furthermore, the polynucleotide may include any additional sequences to the coding sequence encoding the peptide of the present invention. For example, the polynucleotide may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, a polynucleotide may be produced by insertion into an appropriate vector, which may be expressed when transfected into a competent cell. Alternatively, a polynucleotide may be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide may be synthesized using the solid phase techniques, as described in Beaucage S L & Iyer R P, Tetrahedron 1992, 48: 2223-311; Matthes et al., EMBO J. 1984, 3: 801-5.

V. Exosomes

The present invention further provides intracellular vesicles called exosomes, which present complexes formed between the peptides of the present invention and HLA antigens on their surface. Exosomes may be prepared, for example by using the methods detailed in Japanese Patent Application Kohyo Publications No. Hei 11-510507 and WO99/03499, and may be prepared using APCs obtained from patients who are subject to treatment and/or prevention. The exosomes of the present invention may be inoculated as vaccines, similarly to the peptides of the present invention.

The type of HLA antigens included in the complexes must match that of the subject requiring treatment and/or prevention. For example, for Japanese, HLA-A24 and HLA-A2, particularly HLA-A*2402 and HLA-A*0201 and HLA-A*0206 are often appropriate. The use of A24 type or the A2 type that is highly expressed among the Japanese and Caucasian is favorable for obtaining effective results, and subtypes such as A*2402, A*0201 and A*0206 find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution, deletion, or addition of 1, 2, or several amino acids may be performed based on the amino acid sequence of the naturally occurring NEIL3 partial peptide.

In case of using A2 type HLA antigen for the exosome of the present invention, the peptides including the sequence of SEQ ID NOs: 3, 4, 5, 6, 11, 15, 17, 21 and 22 find use.

Alternatively, in case of using the A24 type HLA antigen for the exosome of the present invention, the peptides having a sequence of any one of SEQ ID NOs: 24, 33, 35, 41 and 43 and 61 find use.

VI. Antigen-presenting Cells (APCs)

The present invention also provides isolated APCs that present complexes formed with HLA antigens and the peptides of the present invention on its surface. The APCs may be derived from patients who are subject to treatment and/or prevention, and may be administered as vaccines by themselves or in combination with other drugs including the peptides of the present invention, exosomes, or CTLs.

The APCs are not limited to a particular kind of cells and include DCs, Langerhans cells, macrophages, B cells, and activated T cells, which are known to present proteinaceous antigens on their cell surface so as to be recognized by lymphocytes. Since DC is a representative APC having the strongest CTL inducing activity among APCs, DCs find use as the APCs of the present invention.

For example, the APCs of the present invention may be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. Therefore, the APCs of the present invention may be obtained by collecting the APCs from the subject after administering the peptides of the present invention to the subject. Alternatively, the APCs of the present invention may be obtained by contacting APCs collected from a subject with the peptide of the present invention.

The APCs of the present invention may be administered to a subject for inducing immune response against cancer in the subject by themselves or in combination with other drugs including the peptides, exosomes or CTLs of the present invention. For example, the ex vivo administration may include steps of:

a: collecting APCs from a first subject,
b: contacting with the APCs of step a, with the peptide, and
c: administering the APCs of step b to a second subject.

The first subject and the second subject may be the same individual, or may be different individuals. The APCs obtained by step b may be a vaccine for treating and/or preventing cancer, such as bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

According to an aspect of the present invention, the APCs have a high level of CTL inducibility. In the term of "high level of CTL inducibility", the high level is relative to the level of that by APC contacting with no peptide or peptides which may not induce the CTL. Such APCs having a high level of CTL inducibility may be prepared by a method which includes the step of transferring a polynucleotide encoding the peptide of the present invention to APCs in vitro as well as the method mentioned above. The introduced genes may be in the form of DNAs or RNAs. Examples of methods for introduction include, without particular limitations, various methods conventionally performed in this field, such as lipofection, electroporation, or calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

VII. Cytotoxic T Lymphocytes (CTLs)

A CTL induced against any of the peptides of the present invention strengthens the immune response targeting cancer cells in vivo and thus may be used as vaccines similar to the peptides. Thus, the present invention provides isolated CTLs that are specifically induced or activated by any of the present peptides.

Such CTLs may be obtained by (1) administering the peptide(s) of the present invention to a subject or (2) contacting (stimulating) subject-derived APCs, and CD8 positive cells, or peripheral blood mononuclear leukocytes in vitro with the peptide(s) of the present invention or (3) contacting CD8 positive cells or peripheral blood mononuclear leukocytes in vitro with the APCs or exosomes presenting a complex of an HLA antigen and the peptide on its surface or (4) introducing a gene that includes a polynucleotide encoding a T cell receptor (TCR) subunit binding to the peptide of the present invention. Such APCs or exosomes may be prepared by the methods described above and details of the method of (4) is described bellow in section "VIII. T cell receptor (TCR)".

The CTLs of the present invention may be derived from patients who are subject to treatment and/or prevention, and may be administered by themselves or in combination with other drugs including the peptides of the present invention or exosomes for the purpose of regulating effects. The obtained CTLs act specifically against target cells presenting the peptides of the present invention, for example, the same peptides used for induction. The target cells may be cells that endogenously express NEIL3, such as cancer cells, or cells that are transfected with the NEIL3 gene; and cells that present a peptide of the present invention on the cell surface due to stimulation by the peptide may also serve as targets of activated CTL attack.

VIII. T Cell Receptor (TCR)

The present invention also provides a composition including nucleic acids encoding polypeptides that are capable of forming a subunit of a T cell receptor (TCR), and methods of using the same. The TCR subunits have the ability to form TCRs that confer specificity to T cells against tumor cells presenting NEIL3. By using the known methods in the art, the nucleic acids of alpha- and beta-chains as the TCR subunits of the CTL induced with one or more peptides of the present invention may be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccag-gcattcgcttcat-3') as 5' side primers (SEQ ID NO: 48) and 3-TRa-C primers (5'-tcagctggaccacagccgcagcgt-3') specific to TCR alpha chain C region (SEQ ID NO: 49), 3-TRb-C1 primers (5'-tcagaaatcctttctcttgac-3') specific to TCR beta chain C1 region (SEQ ID NO: 50) or 3-TRbeta-C2 primers (5'-ctagcctctggaatcctttctctt-3') specific to TCR beta chain C2 region (SEQ ID NO: 51) as 3' side primers, but not limited thereto. The derivative TCRs may bind target cells displaying the NEIL3 peptide with high avidity, and optionally mediate efficient killing of target cells presenting the NEIL3 peptide in vivo and in vitro.

The nucleic acids encoding the TCR subunits may be incorporated into suitable vectors, e.g., retroviral vectors. These vectors are well known in the art. The nucleic acids or the vectors including them usefully may be transferred into a T cell, for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR is presented on the surface of the T cell. A specific recognition of the above complex may be confirmed by any known methods, and preferred methods include, for example, HLA multimer staining analysis using HLA molecules and peptides of the present invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay.

Also, the present invention provides CTLs which are prepared by transduction with the nucleic acids encoding the TCR subunits polypeptides that bind to the NEIL3 peptide of, e.g., SEQ ID NOs: 3, 4, 5, 6, 11, 15, 17, 21 and 22 in the context of HLA-A2, and also the peptides of SEQ ID NOs: 24, 33, 35, 41 and 43 in the context of HLA-A24.

The transduced CTLs are capable of homing to cancer cells in vivo, and may be expanded by well known culturing methods in vitro (e.g., Kawakami et al., J. Immunol., 142, 3452-3461 (1989)). The CTLs of the present invention may be used to form an immunogenic composition useful in treating or the prevention of cancer in a patient in need of therapy or protection (WO2006/031221).

IX. Pharmaceutical Substances or Compositions

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g., reducing the proliferation and metastasis of tumors, reducing angiogenesis.

Treating for the prophylaxis of cancer and/or the prevention of postoperative recurrence thereof include(s) any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

Since NEIL3 expression is specifically elevated in cancer such as bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML compared with normal tissue, the peptides of or polynucleotides of the present invention may be used for treating and/or for the prophylaxis of cancer, and/or prevention of postoperative recurrence thereof. Thus, the present invention provides a pharmaceutical substance or composition for treating and/or for the prophylaxis of cancer, and/or prevention of postoperative recurrence thereof, which includes one or more of the peptides, or polynucleotides of the present invention as an active ingredient. Alternatively, the present peptides may be expressed on the surface of any of the foregoing exosomes or cells, such as APCs for the use as pharmaceutical substances or compositions. In addition, the aforementioned CTLs which target any of the peptides of the present invention may also be used as the active ingredient of the present pharmaceutical substances or compositions.

The present pharmaceutical substances or compositions find use as a vaccine. In the present invention, the phrase "vaccine" (also referred to as an immunogenic composition) refers to a substance that has the function to induce anti-tumor immunity upon inoculation into animals.

The pharmaceutical agents or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention
in manufacturing a pharmaceutical composition or substance for treating or preventing cancer or tumor.

Alternatively, the present invention further provides an active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention
for use in treating or preventing cancer of tumor.

Alternatively, the present invention further provides a method or process for manufacturing a pharmaceutical composition or substance for treating or preventing cancer or tumor, wherein the method or process includes the step of formulating a pharmaceutically or physiologically acceptable carrier with an active ingredient selected from among:
 (a) a peptide of the present invention;
 (b) a nucleic acid encoding such a peptide as disclosed herein in an expressible form;

(c) an APC or an exosome presenting a peptide of the present invention on its surface; and (d) a cytotoxic T cell of the present invention as active ingredients.

In another embodiment, the present invention also provides a method or process for manufacturing a pharmaceutical composition or substance for treating or preventing cancer or tumor, wherein the method or process includes the steps of admixing an active ingredient with a pharmaceutically or physiologically acceptable carrier, wherein the active ingredient is selected from among:

(a) a peptide of the present invention;

(b) a nucleic acid encoding such a peptide as disclosed herein in an expressible form;

(c) an APC or an exosome presenting a peptide of the present invention on its surface; and (d) a cytotoxic T cell of the present invention.

According to the present invention, peptides including the amino acid sequence of SEQ ID NO: 3, 4, 5, 6, 11, 15, 17, 21, 22, 24, 33, 35, 41 and 43 have been found to be HLA-A24 or HLA-A2. restricted epitope peptides or the candidates that may induce potent and specific immune response. Therefore, the present pharmaceutical substances or compositions which include any of these peptides with the amino acid sequences of SEQ ID NOs: 3, 4, 5, 6, 11, 15, 17, 21, 22, 24, 33, 35, 41 and 43 are particularly suited for the administration to subjects whose HLA antigen is HLA-A24 or HLA-A2. The same applies to pharmaceutical substances or compositions which include polynucleotides encoding any of these peptides (i.e., the polynucleotides of the present invention).

Cancers to be treated by the pharmaceutical substances or compositions of the present invention are not limited and include any cancer in which NEIL3 is involved (e.g., is overexpressed), for example, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

The present pharmaceutical substances or compositions may contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical substances or compositions of the present invention may optionally include other therapeutic substances as an active ingredient, so long as the substance does not inhibit the antitumoral effect of the active ingredient, e.g., any of the present peptides. For example, formulations may include anti-inflammatory substances or compositions, pain killers, chemotherapeutics, and the like. In addition to other therapeutic substances in the medicament itself, the medicaments of the present invention may also be administered sequentially or concurrently with the one or more other pharmacologic substances or compositions. The amounts of medicament and pharmacologic substance or composition depend, for example, on what type of pharmacologic substance(s) or composition(s) is/are used, the disease being treated, and the scheduling and routes of administration.

It should be understood that in addition to the ingredients particularly mentioned herein, the pharmaceutical substances or compositions of the present invention may include other substances or compositions conventional in the art having regard to the type of formulation in question.

In one embodiment of the present invention, the present pharmaceutical substances or compositions may be included in articles of manufacture and kits containing materials useful for treating the pathological conditions of the disease to be treated, e.g., cancer. The article of manufacture may include a container of any of the present pharmaceutical substances or compositions with a label. Suitable containers include bottles, vials, and test tubes. The containers may be formed from a variety of materials, such as glass or plastic. The label on the container should indicate the substance or composition is used for treating or prevention of one or more conditions of the disease. The label may also indicate directions for administration and so on.

In addition to the container described above, a kit including a pharmaceutical substance or composition of the present invention may optionally further include a second container housing a pharmaceutically-acceptable diluent. It may further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Substances or Compositions Containing the Peptides as the Active ingredient The peptides of the present invention can be administered directly as a pharmaceutical substance or composition, or if necessary, that has been formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical substances or compositions can contain as necessary, stabilizers, suspensions, preservatives, surfactants and such. The pharmaceutical substances or compositions of the present invention can be used for anticancer purposes.

The peptides of the present invention can be prepared in combination, which includes two or more of peptides of the present invention, to induce CTL in vivo. The peptides can be in a cocktail or can be conjugated to each other using standard techniques. For example, the peptides can be chemically linked or expressed as a single fusion polypeptide sequence that may have one or several amino acid(s) as a linker (e.g., Lysine linker: K. S. Kawamura et al. J. Immunol. 2002, 168: 5709-5715). The peptides in the combination can be the same or different. By administering the peptides of the present invention, the peptides are presented in high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of the present invention on their cell surface. These APCs are readministered to the subjects to induce CTLs in the subjects, and as a result, aggressiveness towards the tumor-associated endothelium can be increased.

The pharmaceutical substances or compositions for treatment and/or prevention of cancer, which include any of the peptides of the present invention as the active ingredient, can include an adjuvant so that cellular immunity will be established effectively, or they can be administered with other active ingredients, and they can be administered by formulation into granules. An adjuvant refers to any compound, substance or composition that enhances the immune response against the protein when administered together (or successively) with the protein having immunological activity. An adjuvant that can be applied includes those described in the literature (Clin Microbiol Rev 1994, 7: 277-89). Exemplary adjuvants include aluminum phosphate, aluminum hydroxide, alum, cholera toxin, *salmonella* toxin, Incomplete Freund's adjuvant (IFA), Complete Freund's adjuvant (CFA), ISCOMatrix, GM-CSF, CpG, O/W emulsion, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid.

In some embodiments, the pharmaceutical substances or compositions of the present invention include a component which primes CTL. Lipids have been identified as substances or compositions capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoylS-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1,000 mg, for example, 0.001 mg to 1,000 mg, for example, 0.1 mg to 10 mg, and can be administered once in a few days to few months. One skilled in the art can appropriately select a suitable dose.

(2) Pharmaceutical Substances or Compositions Containing Polynucleotides as Active Ingredient The pharmaceutical substances or compositions of the present invention can also include nucleic acids encoding the peptide(s) disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors. See also, e.g., Wolff et al., Science 1990, 247: 1465-8; U.S. Pat. Nos. 5,580,859; 5,589,466; 5,804,566; 5,739,118; 5,736,524; 5,679,647; and WO 98/04720). Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. Methods Using the Peptides, Exosomes, APCs and CTLs

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical substances or compositions of the present invention can be used for inducing CTLs, and in addition thereto, those including the peptides and polynucleotides can be also be used for inducing APCs as explained below.

(1) Method of Inducing Antigen-Presenting Cells (APCs)

The present invention provides methods of inducing APCs with high CTL inducibility using the peptides or polynucleotides of the present invention.

The methods of the present invention include the step of contacting APCs with the peptides of the present invention in vitro, ex vivo or in vivo. For example, the method contacting APCs with the peptides ex vivo can include steps of:

a: collecting APCs from a subject, and b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or with other peptides of the present invention.

On the other hands, when the peptides of the present invention are administered to a subject, the APCs are contacted with the peptides in vivo, consequently, the APCs with high CTL inducibility are induced in the body of the subject. Thus, the present invention includes administering the peptides of the present invention to a subject. Similarly, when the polynucleotides of the present invention are administered to a subject in an expressible form, the peptides of the present invention are expressed and contacted with APCs in vivo, consequently, the APCs with high CTL inducibility are induced in the body of the subject. Thus, the present invention may also include administering the polynucleotides of the present invention to a subject. "Expressible form" is described above in section "IX. Pharmaceutical substances or compositions, (2) Pharmaceutical substances or compositions containing polynucleotides as the active ingredient".

Furthermore, the present invention may include introducing the polynucleotide of the present invention into an APCs to induce APCs with CTL inducibility. For example, the method can include steps of:

a: collecting APCs from a subject, and b: introducing a polynucleotide encoding peptide of the present invention.

Step b can be performed as described above in section "VI. Antigen-presenting cells".

Alternatively, the present invention provides a method for preparing an antigen-presenting cell (APC) which specifically induces CTL activity against NEIL3, wherein the method can include one of the following steps:

(a) contacting an APC with a peptide of the present invention in vitro, ex vivo or in vivo; and (b) introducing a polynucleotide encoding a peptide of the present invention into an APC.

(2) Method of Inducing CTLs

Furthermore, the present invention provides methods for inducing CTLs using the peptides, polynucleotides, exosomes or APCs of the present invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs may include at least one step selected from the group consisting of:

a) contacting a CD8 positive T cell with an antigen-presenting cell and/or an exosome that presents on its surface a complex of an HLA antigen and a peptide of the preset invention; and b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the methods of the present invention includes the step of administering the peptides, the polynucleotides, the APCs or exosomes of the present invention to a subject.

Alternatively, CTLs can be also induced by using them ex vivo, and after inducing CTL, the activated CTLs can be returned to the subject. For example, the method can include steps of:

a: collecting APCs from a subject;

b: contacting with the APCs of step a, with the peptide; and c: co-culturing the APCs of step b with CD8 positive cells. The APCs to be co-cultured with the CD8 positive cells in above step c can also be prepared by transferring a gene that includes a polynucleotide of the present invention into APCs as described above in section "VI. Antigen-presenting cells"; but are not limited thereto, and any APCs which effectively present on its surface a complex of an HLA antigen and the peptide of the present invention can be used for the present method.

Instead of such APCs, the exosomes that presents on its surface a complex of an HLA antigen and the peptide of the present invention can be also used. Namely, the present invention can include the step of co-culturing exosomes presenting on its surface a complex of an HLA antigen and the peptide of the present invention. Such exosomes can be prepared by the methods described above in section "V. Exosomes".

Furthermore, CTL can be induced by introducing a gene that includes a polynucleotide encoding the TCR subunit binding to the peptide of the present invention into CD8 positive cells. Such transduction can be performed as described above in section "VIII. T cell receptor (TCR)".

In addition, the present invention provides a method or process for manufacturing a pharmaceutical substance or composition inducing CTLs, wherein the method includes the step of admixing or formulating the peptide of the present invention with a pharmaceutically acceptable carrier.

(3) Method of Inducing Immune Response

Moreover, the present invention provides methods of inducing immune response against diseases related to NEIL3. Suitable diseases may include cancer, for example, but not limited to, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

The methods may include the step of administering substance(s) or composition(s) containing any of the peptides of the present invention or polynucleotides encoding them. The present inventive method may also contemplate the administration of exosomes or APCs presenting any of the peptides of the present invention. For details, see the item of "IX. Pharmaceutical substances or compositions", particularly the part describing the use of the pharmaceutical substances or compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical substance or composition inducing immune response, wherein the method may include the step of admixing or formulating the peptide of the present invention with a pharmaceutically acceptable carrier.

Alternatively, the method of the present invention may include the step of administrating a vaccine or a pharmaceutical composition, which contains:
(a) a peptide of the present invention;
(b) a nucleic acid encoding such a peptide as disclosed herein in an expressible form;
(c) an APC or an exosome presenting a peptide of the present invention on its surface; or
(d) a cytotoxic T cell of the present invention.

In the present invention, cancer overexpressing NEIL3 can be treated with these active ingredients. The cancer includes, but is not limited to, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML. Accordingly, prior to the administration of the vaccines or pharmaceutical compositions including the active ingredients, it is preferable to confirm whether the expression level of NEIL3 in the cells or tissues to be treated is enhanced compared with normal cells of the same organ. Thus, in one embodiment, the present invention provides a method for treating cancer (over) expressing NEIL3, which method may include the steps of:
i) determining the expression level of NEIL3 in cells or tissue(s) obtained from a subject with the cancer to be treated;
ii) comparing the expression level of NEIL3 with normal control; and
iii) administrating at least one component selected from the group consisting of (a) to (d) described above to a subject with cancer overexpressing NEIL3 compared with normal control.

Alternatively, the present invention also provides a vaccine or pharmaceutical composition including at least one component selected from the group consisting of (a) to (d) described above, for use in administrating to a subject having cancer overexpressing NEIL3. In other words, the present invention further provides a method for identifying a subject to be treated with the NEIL3 polypeptide of the present invention, which method may include the step of determining an expression level of NEIL3 in subject-derived cells or tissue(s), wherein an increase of the level compared to a normal control level of the gene indicates that the subject may have cancer which may be treated with the NEIL3 polypeptide of the present invention. The method of treating cancer of the present invention will be described in more detail below.

In the context of the present invention, a control level determined from a biological sample that is known to be non-cancerous is referred to as a "normal control level". On the other hand, if the control level is determined from a cancerous biological sample, it is referred to as a "cancerous control level".

A subject to be treated by the present method is preferably a mammal. Exemplary mammals include, but are not limited to, e.g., human, non-human primate, mouse, rat, dog, cat, horse, and cow.

According to the present invention, the expression level of NEIL3 in cells or tissues obtained from a subject may be determined. The expression level can be determined at the transcription (nucleic acid) product level, using methods known in the art. For example, the mRNA of NEIL3 may be quantified using probes by hybridization methods (e.g., Northern hybridization). The detection may be carried out on a chip, an array or as such. The use of an array may be preferable for detecting the expression level of NEIL3. Those skilled in the art can prepare such probes utilizing the sequence information of NEIL3. For example, the cDNA of NEIL3 may be used as the probes. If necessary, the probes may be labeled with a suitable label, such as dyes, fluorescent substances and isotopes, and the expression level of the gene may be detected as the intensity of the hybridized labels.

Furthermore, the transcription product of NEIL3 (e.g., SEQ ID NO: 45) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of NEIL3. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

Alternatively, the translation product may be detected for the diagnosis of the present invention. For example, the quantity of NEIL3 protein (SEQ ID NO: 45) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the NEIL3 protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of NEIL3 gene based on its translation product, the intensity of staining may be measured via immunohistochemical analysis using an antibody against the NEIL3 protein. Namely, in this measurement, strong staining indicates increased presence/level of the protein and, at the same time, high expression level of NEIL3 gene.

The expression level of a target gene, e.g., the NEIL3 gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the cancer cells by using a sample(s) previously collected and stored from a subject(s) whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of NEIL3 gene in samples from subjects whose disease states are known. Furthermore, the control level can be derived from a database of expression patterns from previously tested cells. Moreover, according to an aspect of the present invention, the expression level of NEIL3 gene in a biological sample may be compared to multiple control levels, which are determined from multiple reference samples. It is preferred to use a control level determined from a reference sample derived from a tissue type similar to that of the subject-derived biological sample. Moreover, it is preferred to use the standard value of the expression levels of NEIL3 gene in a population with a known disease state. The standard value may be obtained by any method known in the art. For example, a range of mean+/−2 S.D. or mean+/−3 S.D. may be used as the standard value.

When the expression level of NEIL3 gene is increased as compared to the normal control level, or is similar/equivalent to the cancerous control level, the subject may be diagnosed with cancer to be treated.

More specifically, the present invention provides a method of (i) diagnosing whether a subject suspected to have cancer to be treated, and/or (ii) selecting a subject for cancer treatment, which method may include the steps of:

a) determining the expression level of NEIL3 in cells or tissue(s) obtained from a subject who is suspected to have the cancer to be treated;

b) comparing the expression level of NEIL3 with a normal control level;

c) diagnosing the subject as having the cancer to be treated, if the expression level of NEIL3 is increased as compared to the normal control level; and d) selecting the subject for cancer treatment, if the subject is diagnosed as having the cancer to be treated, in step c).

Alternatively, such a method may include the steps of:

a) determining the expression level of NEIL3 in cells or tissue(s) obtained from a subject who is suspected to have the cancer to be treated;

b) comparing the expression level of NEIL3 with a cancerous control level;

c) diagnosing the subject as having the cancer to be treated, if the expression level of NEIL3 is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from cancer that can be treated with the NEIL3 polypeptide of the present invention, which may also find use in assessing and/or monitoring the efficacy or applicability of a cancer immunotherapy. Preferably, the cancer includes, but is not limited to, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML. More particularly, the kit preferably may include at least one reagent for detecting the expression of the NEIL3 gene in a subject-derived cell, which reagent may be selected from the group of:

(a) a reagent for detecting mRNA of the NEIL3 gene;

(b) a reagent for detecting the NEIL3 protein or the immunologically fragment thereof; and (c) a reagent for detecting the biological activity of the NEIL3 protein.

Suitable reagents for detecting mRNA of the NEIL3 gene may include nucleic acids that specifically bind to or identify the NEIL3 mRNA, such as oligonucleotides which have a complementary sequence to a portion of the NEIL3 mRNA. These kinds of oligonucleotides are exemplified by primers and probes that are specific to the NEIL3 mRNA. These kinds of oligonucleotides may be prepared based on methods well known in the art. If needed, the reagent for detecting the NEIL3 mRNA may be immobilized on a solid matrix. Moreover, more than one reagent for detecting the NEIL3 mRNA may be included in the kit.

On the other hand, suitable reagents for detecting the NEIL3 protein or the immunologically fragment thereof may include antibodies to the NEIL3 protein or the immunologically fragment thereof. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the NEIL3 protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the NEIL3 protein may be included in the kit.

The kit may contain more than one of the aforementioned reagents. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers may include bottles, vials, and test tubes. The containers may be formed from a variety of materials, such as glass or plastic.

In an embodiment of the present invention, when the reagent is a probe against the NEIL3 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of NEIL3 mRNA present in the sample. The detection sites may be configured in any suitably detectable shape and are typically in the shape of a bar or dot spanning the width of a test strip.

The kit of the present invention may further include a positive control sample or NEIL3 standard sample. The positive control sample of the present invention may be prepared by collecting NEIL3 positive samples and then assaying their NEIL3 levels. Alternatively, a purified NEIL3 protein or polynucleotide may be added to cells that do not express NEIL3 to form the positive sample or the NEIL3 standard sample. In the present invention, purified NEIL3 may be a recombinant protein. The NEIL3 level of the positive control sample is, for example, more than the cut off value.

In one embodiment, the present invention further provides a diagnostic kit including, a protein or a partial protein thereof capable of specifically recognizing the antibody of the present invention or the fragment thereof.

Examples of the partial peptide of the protein of the present invention include polypeptides consisting of at least 8, preferably 15, and more preferably 20 contiguous amino acids in the amino acid sequence of the protein of the present invention. Cancer can be diagnosed by detecting an antibody in a sample (e.g., blood, tissue) using a protein or a peptide (polypeptide) of the present invention. The method for preparing the protein of the present invention and peptides are as described above.

Diagnostic method for cancer can be done by determining the difference between the amount of anti-NEIL3 antibody and that in the corresponding control sample as describe above. The subject is suspected to be suffering from cancer, if cells or tissues of the subject contain antibodies against the expression products (NEIL3) of the gene and the quantity of the anti-NEIL3 antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides a method or diagnostic agents for evaluating immunological response of subject by using peptide epitopes as described herein. In one embodiment of the invention, HLA restricted peptides as described herein may be used as reagents for evaluating or predicting an immune response of a subject. The immune response to be evaluated may be induced by contacting an immunogen with immunocompetent cells in vitro or in vivo.

In some embodiments, any substances or compositions that may result in the production of antigen specific CTLs that recognize and bind to the peptide epitope(s) may be employed as the reagent. The peptide reagents may need not to be used as the immunogen. Assay systems that are used for such an analysis include relatively recent technical developments such as tetramers, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer consisting of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J. Exp. Med. 174: 1565-1570, 1991) including peptides of the present invention. For example, patient PBMC samples from individuals with cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOLOGY, Wiley/Greene, NY; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

Alternatively, the invention also provides a number of uses, some of which are described herein. For instance, the present invention provides a method for diagnosing or detecting a disorder characterized by expression of a NEIL3 immunogenic polypeptide. These methods involve determining expression of a NEIL3 HLA binding peptide, or a complex of a NEIL3 HLA binding peptide and an HLA class I molecule in a biological sample. The expression of a peptide or complex of peptide and HLA class I molecule can be determined or detected by assaying with a binding partner for the peptide or complex. In an preferred embodiment, a binding partner for the peptide or complex may be an antibody recognizes and specifically bind to the peptide. The expression of NEIL3 in a biological sample, such as a tumor biopsy, can also be tested by standard PCR amplification protocols using NEIL3 primers. An example of tumor expression is presented herein and further disclosure of exemplary conditions and primers for NEIL3 amplification can be found in WO2003/27322.

Preferably, the diagnostic methods involve contacting a biological sample isolated from a subject with an agent specific for the NEIL3 HLA binding peptide to detect the presence of the NEIL3 HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and NEIL3 HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The diagnostic method of the present invention can be performed in either or both of in vivo and in vitro. Accordingly, biological sample can be located in vivo or in vitro in the present invention. For example, the biological sample can be a tissue in vivo and the agent specific for the NEIL3 immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

XI. Antibodies

The present invention further provides antibodies that bind to the peptide of the present invention. Preferred antibodies specifically bind to the peptide of the present invention and will not bind (or will bind weakly) to non-peptide of the present invention. Alternatively, antibodies bind to the peptide of the invention as well as the homologs thereof. Antibodies against the peptide of the invention can find use in cancer diagnostic and prognostic assays, and imaging methodologies. Similarly, such antibodies can find use in the treatment, diagnosis, and/or prognosis of other cancers, to the extent NEIL3 is also expressed or overexpressed in cancer patient. Moreover, intracellularly expressed antibodies (e.g., single chain antibodies) may therapeutically find use in treating cancers in which the expression of NEIL3 is involved, such as, for example, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

The present invention also provides various immunological assay for the detection and/or quantification of NEIL3 protein (SEQ ID NO: 45) or fragments thereof including polypeptide consisting of amino acid sequences selected from the group consisting of SEQ ID NOs: 3, 4, 5, 6, 11, 15, 17, 21, 22, 24, 33, 35, 41 and 43. Such assays may include one or more anti-NEIL3 antibodies capable of recognizing and binding a NEIL3 protein or fragments thereof, as appropriate. In the present invention, anti-NEIL3 antibodies binding to NEIL3 polypeptide preferably recognize polypeptide consisting of amino acid sequences selected from the group consisting of SEQ ID NOs: 3, 4, 5, 6, 11, 15, 17, 21, 22, 24, 33, 35, 41 and 43. A binding specificity of antibody can be confirmed with inhibition test. That is, when the binding between an antibody to be analyzed and full-length of NEIL3 polypeptide is inhibited under presence of any fragment polypeptides consisting of amino acid sequence of SEQ TD NOs: 3, 4, 5, 6, 11, 15, 17, 21, 22, 24, 33, 35, 41 and 43, it is shown that this antibody specifically binds to the fragment. In the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing NEIL3 are also provided by the invention, including, but not limited to, radioscintigraphic imaging methods using labeled antibodies of the present invention. Such assays can clinically find use in the detection, monitoring, and prognosis of NEIL3 expressing cancers such as bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

The present invention also provides an antibody that binds to the peptide of the invention. The antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a NEIL3 peptide. In a preferred embodiment, antibody of the present invention can recognize fragment peptides of NEIL3 consisting of amino acid sequence selected from the group consisting of SEQ ID NOs: 3, 4, 5, 6, 11, 15, 17, 21, 22, 24, 33, 35, 41 and 43. Methods for synthesizing oligopeptide are well known in the arts. After the synthesis, peptides may be optionally purified prior to use as immunogen. In the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primates may be used. Animals of Rodentia include, for example, mouse, rat and hamster. Animals of Lagomorpha include, for example, rabbit. Animals of Primates include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178:

476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239: 1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F. F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. Vectors and Host Cells

The present invention also provides a vector and host cell into which a nucleotide encoding the peptide of the present invention is introduced. A vector of the present invention can find use to keep a nucleotide, especially a DNA, of the present invention in host cell, to express the peptide of the present invention, or to administer the nucleotide of the present invention for gene therapy.

When E. coli is a host cell and the vector is amplified and produced in a large amount in E. coli (e.g., JM109, DH5 alpha, HB101 or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB1011 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or N1H3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

XIII. A Method for Diagnosing Cancer:

The present invention also provides a method of diagnosing cancer. The expression of NEIL3 was found to be specifically elevated in several kinds of cancer cells (Table 1 and FIG. 5). Therefore, the genes identified herein as well as their transcription and translation products find diagnostic utility as markers for cancer and by measuring the expression of NEIL3 in a biological sample (e.g., a cell sample), cancer can be diagnosed. Specifically, the present invention provides a method for diagnosing cancer by determining the expression level of NEIL3 in the subject. Cancers that can be diagnosed by the present method include, but nor limited to, bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML. Furthermore, NSCLC, including lung adenocarcinoma and lung squamous cell carcinoma (SCC), can also be diagnosed or detected by the present invention.

According to the present invention, an intermediate result for examining the condition of a subject may be provided. Such intermediate result may be combined with additional information to assist a doctor, nurse, or other practitioner to diagnose that a subject suffers from the disease. Alternatively, the present invention may be used to detect cancerous cells in a subject-derived tissue, and provide a doctor with useful information to diagnose that the subject suffers from the disease.

Specifically, the present invention provides the following methods [1] to [10]:

[1] A method for diagnosing cancer, said method including the steps of:

(a) detecting the expression level of the gene encoding the amino acid sequence of NEIL3 in a biological sample; and (b) correlating an increase in the expression level detected as compared to a normal control level of the gene to the presence of disease.

[2] The method of [1], wherein the expression level is at least 10% greater than the normal control level.

[3] The method of [1], wherein the expression level is detected by a methods selected from among:

(a) detecting an mRNA including the sequence of NEIL3, (b) detecting a protein including the amino acid sequence of NEIL3, and (c) detecting a biological activity of a protein including the amino acid sequence of NEIL3.

[4] The method of [1], wherein the cancer is selected from a group of bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

[5] The method of [3], wherein the expression level is determined by detecting hybridization of a probe to a gene transcript of the gene.

[6] The method of [3], wherein the expression level is determined by detecting the binding of an antibody against the protein encoded by a gene as the expression level of the gene.

[7] The method of [1], wherein the biological sample includes biopsy, sputum, blood, pleural effusion or urine.

[8] The method of [1], wherein the subject-derived biological sample includes an epithelial cell.

[9] The method of [1], wherein the subject-derived biological sample includes a cancer cell.

[10] The method of [1], wherein the subject-derived biological sample includes a cancerous epithelial cell.

Alternatively, the present invention provides a method for detecting or identifying cancer cells in a subject-derived tissue sample, said method including the step of determining the expression level of the NEIL3 gene in a subject-derived biological sample, wherein an increase in said expression level as compared to a normal control level of said gene indicates the presence or suspicion of cancer cells in the tissue. Such result may be combined with additional information to assist a doctor, nurse, or other healthcare practitioner in diagnosing a subject as afflicted with the disease. In other words, the present invention may provide a doctor with useful information to diagnose a subject as afflicted with the disease. For example, according to the present invention, when there is doubt regarding the presence of cancer cells in the tissue obtained from a subject, clinical decisions can be reached by considering the expression level of the NEIL3 gene, plus a different aspect of the disease including tissue pathology, levels of known tumor marker(s) in blood, and clinical course of the subject, etc.

For example, some well-known diagnostic bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML markers in blood are as follows:

bladder cancer; SCC, TPA, or IAP
breast cancer; BCA225, TPA, CEA, IAP, or CA15-3
cervical cancer; SCC, TPA, or CA125
cholangiocellular carcinoma; CA 19-9, or CEA
colorectal cancer; CEA
endometriosis; CA125
esophagus cancer; CEA, DUPAN-2, TAP, NSE, SCC, SLX, or Span-1
liver cancer; AFP, or ICDH
NSCLC; CEA
osteosarcoma; ALP
pancreatic cancer; BFP, CA19-9, CA125, or CEA
prostate cancer; PSA, or PAP
renal cell carcinoma; IAP
SCLC; ProGRP or NSE
AML; TK activity
CML; TK activity Namely, in this particular embodiment of the present invention, the outcome of the gene expression analysis serves as an intermediate result for further diagnosis of a subject's disease state.

In another embodiment, the present invention provides a method for detecting a diagnostic marker of cancer, said method including the step of detecting the expression of the NEIL3 gene in a subject-derived biological sample as a diagnostic marker of bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML, but not limited thereto.

The method of diagnosing cancer will be described in more detail below.

A subject to be diagnosed by the present method is preferably a mammal. Exemplary mammals include, but are not limited to, e.g., human, non-human primate, mouse, rat, dog, cat, horse, and cow.

It is preferred to collect a biological sample from the subject to be diagnosed to perform the diagnosis. Any biological material can be used as the biological sample for the determination so long as it includes the objective transcription or translation product of NEIL3. The biological samples include, but are not limited to, bodily tissues and fluids, such as blood, sputum and urine. In some embodiments, the biological sample contains a cell population comprising an epithelial cell, more preferably a cancerous epithelial cell or an epithelial cell derived from tissue suspected to be cancerous. Further, if necessary, the cell may be purified from the obtained bodily tissues and fluids, and then used as the biological sample.

According to the present invention, the expression level of NEIL3 in the subject-derived biological sample is determined. The expression level can be determined at the transcription (nucleic acid) product level, using methods known in the art. For example, the mRNA of NEIL3 may be quantified using probes by hybridization methods (e.g., Northern hybridization). The detection may be carried out on a chip or an array. The use of an array is preferable for detecting the expression level of a plurality of genes (e.g., various cancer specific genes) including NEIL3. Those skilled in the art can prepare such probes utilizing the sequence information of the NEIL3 (SEQ ID NO: 44; GenBank accession number: NM_018248). For example, the cDNA of NEIL3 may be used as the probes. If necessary, the probe may be labeled with a suitable label, such as dyes, fluorescent and isotopes, and the expression level of the gene may be detected as the intensity of the hybridized labels.

Furthermore, the transcription product of NEIL3 may be quantified using primers by amplification-based detection methods (e.g., RT-PCR). Such primers can also be prepared based on the available sequence information of the gene. For example, the primers (SEQ ID NOs: 46 and 47) used in the Example may be employed for the detection by RT-PCR or Northern blot, but the present invention is not restricted thereto.

Specifically, a probe or primer used for the present method hybridizes under stringent, moderately stringent, or low stringent conditions to the mRNA of NEIL3.

Alternatively, the translation product may be detected for the diagnosis of the present invention. For example, the quantity of NEIL3 protein may be determined. A method for determining the quantity of the protein as the translation product includes immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment retains the binding ability to NEIL3 protein. Methods to prepare these kinds of antibodies for the detection of proteins are well known in the art, and any method may be employed in the present invention to prepare such antibodies and equivalents thereof.

As another method to detect the expression level of NEIL3 gene based on its translation product, the intensity of staining may be observed via immunohistochemical analysis using an antibody against NEIL3 protein. Namely, the observation of strong staining indicates increased presence of the protein and at the same time high expression level of NEIL3 gene.

Moreover, in addition to the expression level of NEIL3 gene, the expression level of other cancer-associated genes, for example, genes known to be differentially expressed in cancer may also be determined to improve the accuracy of the diagnosis.

The expression level of cancer marker gene including NEIL3 gene in a biological sample can be considered to be increased if it increases from the control level of the corresponding cancer marker gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the test biological sample by using a sample(s) previously collected and stored from a subject/subjects whose disease state (cancerous or non-cancerous) is/are known. Alternatively, the control level may be determined by a statistical method based on the results obtained by analyzing previously determined expression level(s) of NEIL3 gene in samples from subjects whose disease state are known. Furthermore, the control level can be a database of expression patterns from previously tested cells. Moreover, according to an aspect of the present invention, the expression level of NEIL3 gene in a biological sample may be compared to multiple control levels, which control levels are determined from multiple reference samples. It is preferred to use a control level determined from a reference sample derived from a tissue type similar to that of the patient-derived biological sample. Moreover, it is preferred, to use the standard value of the expression levels of NEIL3 gene in a population with a known disease state. The standard value may be obtained by any method known in the art. For example, a range of mean+/−2 S.D. or mean+/−3 S.D. may be used as standard value.

When the expression level of NEIL3 gene is increased as compared to the normal control level or is similar to the cancerous control level, the subject may be diagnosed to be suffering from or at a risk of developing cancer. Furthermore, in the case where the expression levels of multiple cancer-related genes are compared, a similarity in the gene expression pattern between the sample and the reference which is cancerous indicates that the subject is suffering from or at a risk of developing cancer. Difference between the expression levels of a test biological sample and the control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention will be further described in the following examples, which do not limit the scope of the invention described in the claims.

EXAMPLES

Materials and Methods
Cell Lines

T2 (HLA-A2), human B-lymphoblastoid cell line, COST and African green monkey kidney cell line, were purchased from ATCC and PSCCA0922 (HLA-*A0206) was purchased from Japan Health Sciences Foundation. TISI, HLA-A*2402-positive B-lymphoblastoid cell line, was purchased from the IHWG Cell and Gene Bank (Seattle, Wash.).

Candidate Selection of Peptides Derived from NEIL3

9-mer and 10-mer peptides derived from NEIL3 that bind to HLA-A*0201 molecule were predicted using binding prediction software "BIMAS" (www-bimas.cit.nih.gov/molbio/hla_bind) (Parker et al. (J Immunol 1994, 152(1): 163-75), Kuzushima et al. (Blood 2001, 98(6): 1872-81)). 9-mer and 10-mer peptides derived from NEIL3 that bind to HLA-A*2402 molecule were predicted using "NetMHC3.0" binding prediction server (www.cbs.dtu.dk/services/NetMHC/) (Buus et al. (Tissue Antigens., 62:378-84, 2003), Nielsen et al. (Protein Sci., 12:1007-17, 2003, Bioinformatics, 20(9): 1388-97, 2004)). These peptides were synthesized by Biosynthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*0201 or HLA-A*0206 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1,000 U/ml of granulocyte-macrophage colony-stimulating factor (GM-CSF) (R&D System) and 1,000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiated (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTL was tested against peptide-pulsed T2 or PSCCA0922 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 I/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-Dwell of AIM-V Medium containing 5% AS. 50 micro-1/well of TL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed T2 ($1 \times 10^4$/well) was prepared as stimulator cells. Cultured cells in 48 wells were used as responder cells. IFN-gamma ELISPOT assay and IFN-gamma ELISA assay were performed under manufacture procedure.

Plasmid Transfection

The cDNA encoding an open reading frame of target genes, HLA-A*0201, HLA-A*0206 or HLA-A*2402 was amplified by PCR. The PCR-amplified product was cloned into a vector. The plasmids were transfected into COST, which is the target genes and HLA-A2- and A24-negative cell line, using lipofectamine 2000 (Invitrogen) according to the manufacturer's recommended procedures. After 2 days from transfection, the transfected cells were harvested with versene (Invitrogen) and used as the target cells ($5 \times 10^4$ cells/well) for CTL activity assay.

Semi-quantitative RT-PCR Analysis

Total RNA was extracted with a Qiagen RNeasy kit (Qiagen) or Trizol reagent (Life Technologies, Inc.) according to the manufacturers' protocols. Ten-microgram aliquots of total RNA were reversely transcribed for single-stranded cDNAs using poly $dT_{12-18}$ primer (Amersham Pharmacia Biotech) with Superscript II reverse transcriptase (Life Technologies). Each single-stranded cDNA preparation was diluted for subsequent PCR amplification by standard RT- PCR experiments carried out in 12 micro-1 volumes of PCR buffer (TAKARA). Amplification proceeded for 4 min at 94 degrees C. for denaturing, followed by 28 cycles of 94 degrees C. for 30 s, 60 degrees C. for 30 s, and 72 degrees C. for 60 s, in the GeneAmp PCR system 9700 (Perkin-Elmer, Foster City, Calif.). Primer sequences were; for NEIL3: forward, 5'-TTGGTCCTCCTCT-GTTTCATAGA-3' (SEQ ID NO: 46) and reverse, 5'-GCTTCTCCCCAGTTACAA-GAGAC-3' (SEQ ID NO: 47).

Results

Enhanced NEIL3 Expression in Cancers

The global gene expression profile data obtained from various cancers using cDNA-microarray revealed that NEIL3 (GenBank Accession No. NM_018248; SEQ ID No: 44) expression was elevated. NEIL3 expression was validly elevated in 4 out of 20 AMLs, 5 out of 6 bladder cancers, 10 out of 11 breast cancers, 8 out of 8 cervical cancers, 1 out of 1 cholangiocellular carcinoma, 12 out of 12 CMLs, 3 out of 6 colorectal cancers, 1 out of 1 endometriosis, 4 out of 8 esophagus cancers, 6 out of 10 liver cancers, 7 out of 7 NSCLCs, 16 out of 16 osteosarcomas, 1 out of 1 pancreatic cancer, 10 out of 10 prostate cancers, 2 out of 2 renal carcinomas, 12 out of 12 SCLCs and 12 out of 12 soft tissue tumors as compared with corresponding normal tissue (Table 1).

TABLE 1

Ratio of cases observed up-regulation of NEIL3 in cancerous tissue as compared with normal corresponding tissue.

| Cancers | Ratio |
| --- | --- |
| AML | 4/20 |
| Bladder Cancer | 5/6 |
| Breast Cancer | 10/11 |
| Cervical Cancer | 8/8 |
| Cholangiocellular Carcinoma | 1/1 |
| CML | 12/12 |
| Colorectal Cancer | 3/6 |
| Endometriosis | 1/1 |
| Esophagus Cancer | 4/8 |
| Liver cancer | 6/10 |
| NSCLC | 7/7 |
| Osteosarcoma | 16/16 |
| Pancreatic Cancer | 1/1 |
| Prostate Cancer | 10/10 |
| Renal Carcinoma | 2/2 |
| SCLC | 12/12 |
| Soft Tissue Tumor | 12/12 |

Experimental 1

Prediction of HLA-A2 Binding Peptides Derived From NEIL3

Table 2 shows the HLA-A2 binding peptides of NEIL3 in the order of high binding affinity. A total of 23 peptides with potential HLA-A2 binding ability were selected and examined to determine the epitope peptides (Table 2).

TABLE 2

HLA-A2 binding peptides derived from NEIL3

| | Start position | Sequence | score | SEQ ID NO. |
| --- | --- | --- | --- | --- |
| NEIL3-A2-9 mer | 64 | VLSLFNGYV | 321.3 | 1 |
| | 84 | FMYFGPKAL | 227.1 | 2 |
| | 585 | KQCNFFQWA | 70.0 | 3 |
| | 127 | LICFFDSSV | 61.8 | 4 |
| | 416 | FQNSPPASV | 32.4 | 5 |
| | 71 | YVYSGVETL | 31.0 | 6 |
| | 41 | RLAASTVVV | 28.5 | 7 |
| | 34 | SLQGRALRL | 21.4 | 8 |
| | 298 | IISWTSSRV | 16.3 | 9 |
| | 291 | KLPTRNTII | 15.0 | 10 |
| | 271 | RMTYFCPHC | 13.6 | 11 |
| | 492 | NMTDGPRTL | 12.7 | 12 |
| NEIL3-A2-10 mer | 18 | VLPGQAVTGV | 271.9 | 13 |
| | 212 | QLTDEQTHHL | 201.4 | 14 |
| | 198 | ALFDSGLHPA | 173.3 | 15 |
| | 181 | LMDQNVLPGV | 78.6 | 16 |
| | 340 | CLTSRPIDSV | 78.4 | 17 |
| | 239 | GLALSKHYKV | 69.6 | 18 |
| | 55 | ALNNDSSQNV | 69.6 | 19 |
| | 63 | NVLSLFNGYV | 61.2 | 20 |
| | 590 | FQWAENGPGI | 40.4 | 21 |
| | 378 | KINRKTAFGT | 20.8 | 22 |
| | 569 | GPNNGKNFFV | 14.5 | 23 |

Start position indicates the number of amino acid residue from the N-terminus of NEIL3.
Binding score is derived from "BIMAS".

CTL Induction with the Predicted Peptides from NEIL3 Restricted with HLA-A*0201 or 0206 and Establishment for CTL Lines Stimulated with NEIL3 Derived Peptides CTLs for those peptides derived from NEIL3 were generated according to the protocols as described in "Materials and Methods". Peptide specific CTL activity was determined by IFN-gamma ELISPOT assay (FIGS. 1a-j). It showed that the well number #8 stimulated with NEIL3-A2-9-585 (SEQ ID NO: 3) (a), #2 with NEIL3-A2-9-127 (SEQ ID NO: 4) (b), #4 and 5 with NEIL3-A2-9-416 (SEQ ID NO: 5) (c), #3 with NEIL3-A2-9-71 (SEQ ID NO: 6) (d), #1 with NEIL3-A2-9-271 (SEQ ID NO: 11) (e), #3 with NEIL3-A2-10-198 (SEQ ID NO: 15) (f), #1 with NEIL3-A2-10-340 (SEQ ID NO: 17) (g), #2 and 3 with NEIL3-A2-10-590 (SEQ ID NO: 21) (h) and #6 with NEIL3-A2-10-378 (SEQ ID NO: 22) (i) demonstrated potent IFN-gamma production as compared to the control wells. In addition, the well number #9, 10, 12 and 13 with NEIL3-A2-9-416 (SEQ ID NO: 5) (j) demonstrated potent IFN-gamma production against peptide pulsed A0206 positive PSCCA0922 cells. Furthermore, the cells in the positive well number #8 stimulated with NEIL3-A2-9-585 (SEQ ID NO: 3), #2 with NEIL3-A2-9-127 (SEQ ID NO: 4), #4 and 5 with NEIL3-A2-9-416 (SEQ ID NO: 5), #3 with NEIL3-A2-9-71 (SEQ ID NO: 6), #1 with NEIL3-A2-9-271 (SEQ ID NO: 11), #3 with NEIL3-A2-10-198 (SEQ ID NO: 15) and, #2 and 3 with NEIL3-A2-10-590 (SEQ ID NO: 21) were expanded and established CTL lines, and #10 and 12 with NEIL3-A2-9-416 for A0206 (SEQ ID NO: 5) were also expanded and established CTL lines. CTL activity of those CTL lines was determined by TEN-gamma ELISA assay (FIGS. 2a-k). It showed that all CTL lines demonstrated potent IFN-gamma production against the target cells pulsed with corresponding peptide as compared to target cells without peptide pulse. On the other hand, no CTL lines could be established by stimulation with other peptides shown in Table 2, despite those peptide had possible binding activity with HLA-A*0201 (data not shown). As a result, it indicated that 7 peptides derived from NEIL3 were screened as the peptides could induce potent CTLs.

Establishment of CTL Clones Against NEIL3 Specific Peptides

Figure 3:
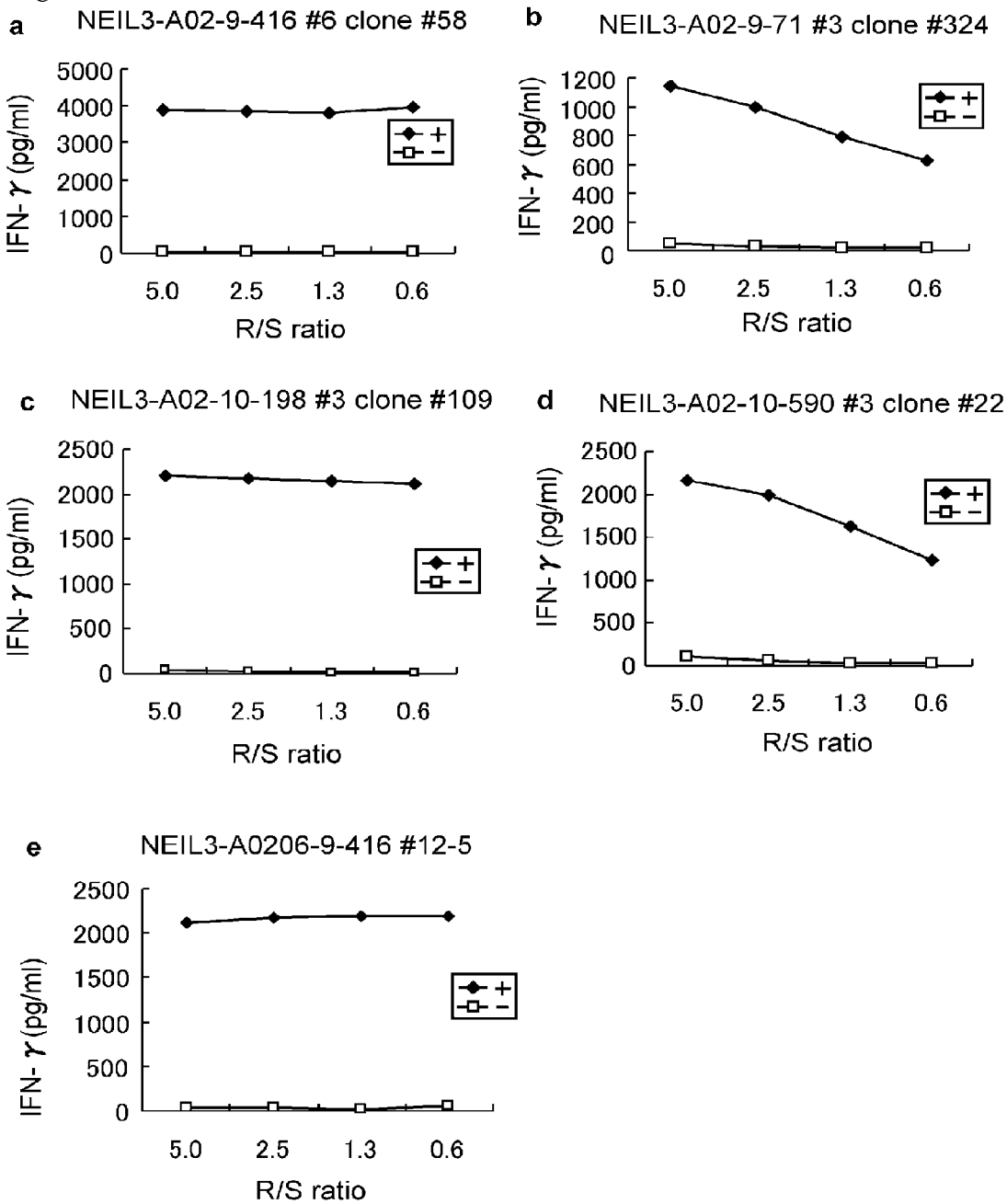
[FIG. 3]

CTL clones were established by limiting dilution from CTL lines as described in "Materials and Methods", and IFN-gamma production from CTL clones against target cells pulsed peptide were determined by IFN-gamma ELISA assay. Potent IFN-gamma productions were determined from CTL clones stimulated with SEQ ID NO: 5, SEQ ID NO: 6, SEQ ID NO: 15 and SEQ ID NO: 21 in FIG. 3.

Specific CTL Activity Against Target Cells Exogenously Expressing NEIL3 and HLA-A*0201 or HLA-A*0206

Figures 2, 4:
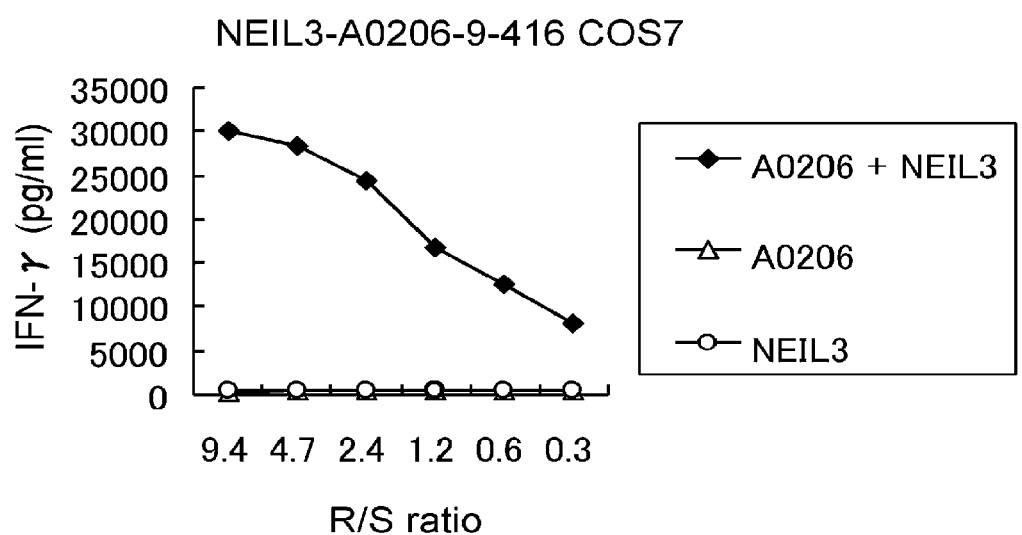
Figure 6:
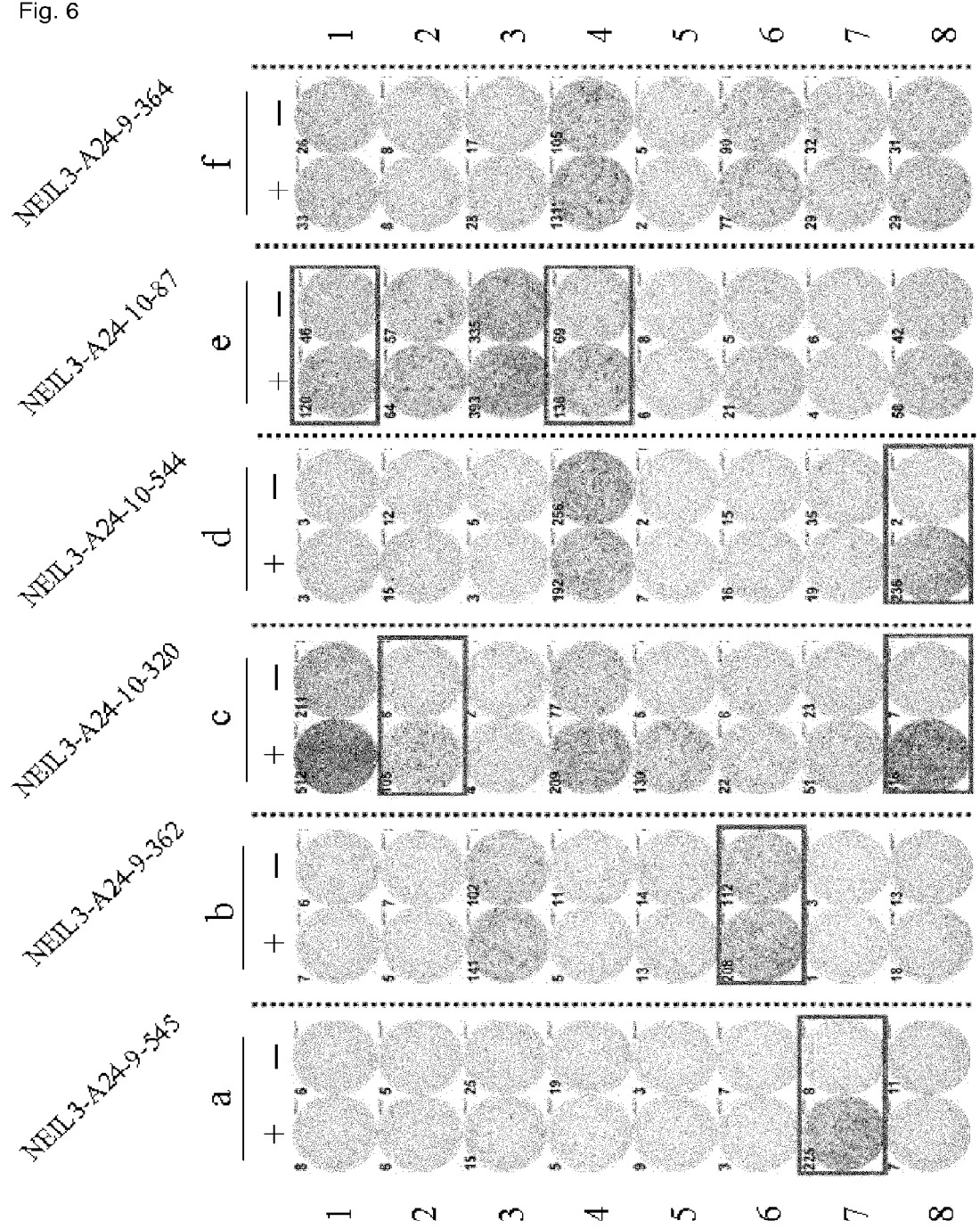
[FIG. 6]
Figure 7:
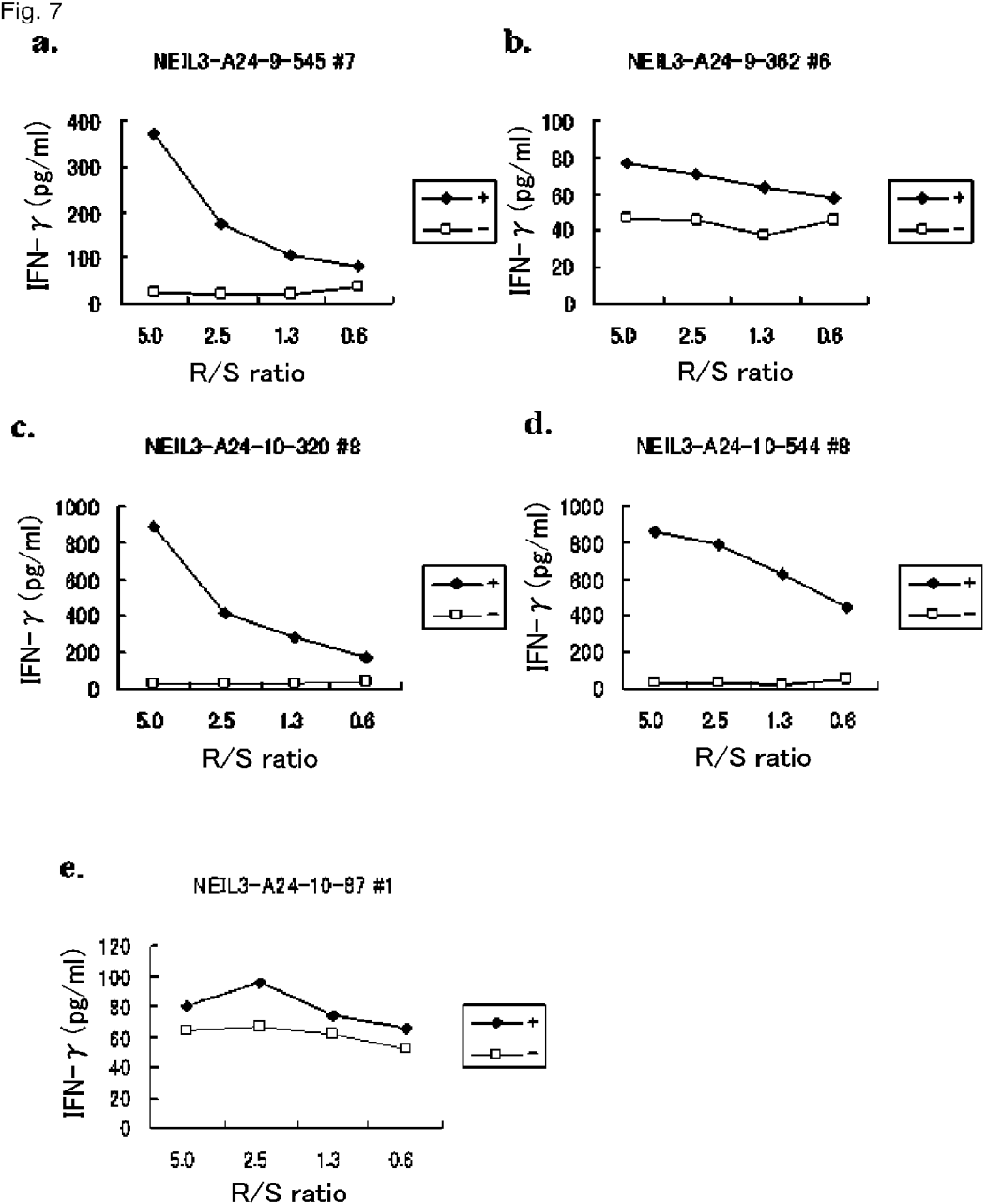
[FIG. 7]

The established CTL lines raised against these peptides were examined for their ability to recognize target cells that endogenously express NEIL3 and HLA-A*0201 or HLA-A*0206 molecule. Specific CTL activity against COS7 cells which transfected with both the full length of NEIL3 and HLA-A*0201 or HLA-A*0206 molecule gene (a specific model for the target cells that exogenously express NEIL3 and HLA-A*0201 or HLA-A*0206 gene) was tested using the CTL lines raised by corresponding peptide as the effecter cells. COS7 cells transfected with either full length of NEIL3, HLA-A* 0201 or HLA-A*0206gene were prepared as control. In FIG. 4, the CTLs stimulated with SEQ ID NO: 5, SEQ ID NO: 6 and SEQ ID NO: 15 showed potent CTL activity against COS7 cells expressing both NEIL3 and HLA-A* 0201, and the CTLs stimulated with SEQ ID NO: 5 also showed potent CTL activity against COS7 cells expressing both NEIL3 and HLA-A* 0206. On the other hand, no significant specific CTL activity was detected against the controls. Thus, these data clearly demonstrated that NEIL3-A2-9-416 (SEQ ID NO: 5), NEIL3-A2-9-71 (SEQ ID NO: 6) and NEIL3-A2-10-198 (SEQ ID NO: 15) were naturally expressed on the target cells with HLA-A*0201 molecule and were recognized by the CTLs, and NEIL3-A2-9-416 (SEQ ID NO: 5) was also naturally expressed on the target cells with HLA-A*0206 molecule and was recognized by the CTLs. These results indicated that these peptides derived from NEIL3 may be available to apply the cancer vaccines for patients with NEIL3 expressing tumors.

Homology Analysis of Antigen Peptides

The CTLs stimulated with NEIL3-A2-9-585 (SEQ ID NO: 3), NEIL3-A2-9-127 (SEQ ID NO: 4), NEIL3-A2-9-416 (SEQ ID NO: 5), NEIL3-A2-9-71 (SEQ ID NO: 6), NEIL3-A2-9-271 (SEQ ID NO: 11), NEIL3-A2-10-198 (SEQ ID NO: 15), NEIL3-A2-10-340 (SEQ ID NO: 17), NEIL3-A2-10-590 (SEQ ID NO: 21) and NEIL3-A2-10-378 (SEQ ID NO: 22) showed significant and specific CTL activity. This result may be due to the fact that the sequences of NEIL3-A2-9-585 (SEQ ID NO: 3), NEIL3-A2-9-127 (SEQ ID NO: 4), NEIL3-A2-9-416 (SEQ ID NO: 5), NEIL3-A2-9-71 (SEQ ID NO: 6), NEIL3-A2-9-271 (SEQ ID NO: 11), NEIL3-A2-10-198 (SEQ ID NO: 15), NEIL3-A2-10-340 (SEQ ID NO: 17), NEIL3-A2-10-590 (SEQ ID NO: 21) and NEIL3-A2-10-378 (SEQ ID NO: 22) are homologous to peptides derived from other molecules that are known to sensitize the human immune system. To exclude this possibility, homology analyses were performed for these peptide sequences using as queries the BLAST algorithm (www.ncbi.nlm.nih.gov/blast/blast.cgi) which revealed no sequence with significant homology. The results of homology analyses indicate that the sequences of NEIL3-A2-9-585 (SEQ ID NO: 3), NEIL3-A2-9-127 (SEQ ID NO: 4), NEIL3-A2-9-416 (SEQ ID NO: 5), NEIL3-A2-9-71 (SEQ ID NO: 6), NEIL3-A2-9-271 (SEQ ID NO: 11), NEIL3-A2-10-198 (SEQ ID NO: 15), NEIL3-A2-10-340 (SEQ ID NO: 17), NEIL3-A2-10-590 (SEQ ID NO: 21) and NEIL3-A2-10-378 (SEQ ID NO: 22) are unique and thus, there is little possibility, to our best knowledge, that these molecules raise unintended immunologic response to some unrelated molecule.

In conclusion, novel HLA-A2 epitope peptides derived from NEIL3 were identified. Furthermore, it was demonstrated that epitope peptides of NEIL3 may be applicable for cancer immunotherapy.

Elevated Expression of NEIL3 in a Wide Range of Human Cancers

Subsequent semi-quantitative RT-PCR analysis revealed enhanced NEIL3 expression in 7 of 8 ICCs that were subjected to the microarray analysis (FIG. 5a).

To confirm the expression pattern of this gene in liver cancers, the inventers performed semi-quantitative RT-PCR analysis using clinical liver cancer specimens and normal human tissues including normal liver cells. As a result, the inventers found that NEIL3 whose expression showed the elevated expression in 7 of 8 clinical liver cancer specimens (poorly-differentiated lesions) compared to normal liver cells (FIG. 5a), and was overexpressed in 5 of 5 HCC cell lines and not expressed in other normal tissues (FIG. 5b).

Experimental 2

Prediction of HLA-A24 Binding Peptides Derived from NEIL3

Table 3a and 3b show the HLA-A24 binding 9mer and 10mer peptides of NEIL3 in the order of high binding affinity. A total of 21 peptides with potential HLA-A24 binding ability were selected and examined to determine the epitope peptides.

TABLE 3a

HLA-A24 binding 9 mer peptides derived from NEIL3

| Start Position | Amino acid sequence | Kd (nM) | SEQ ID NO |
|---|---|---|---|
| 545 | EWADLSFPF | 10 | 24 |
| 364 | KYPCNTFGK | 314 | 25 |
| 320 | HWTCVVCTT | 456 | 26 |
| 86 | YFGPKALRI | 779 | 27 |
| 60 | SSQNVLSLF | 878 | 28 |
| 591 | QWAENGPGI | 1038 | 29 |
| 560 | STMKTVLKI | 1250 | 30 |
| 192 | NIIKNEALF | 3681 | 31 |

TABLE 3a-continued

HLA-A24 binding 9 mer peptides derived from NEIL3

| Start Position | Amino acid sequence | Kd (nM) | SEQ ID NO |
|---|---|---|---|
| 186 | VLPGVGNII | 7297 | 32 |
| 362 | LMKYPCNTF | 9549 | 33 |
| 445 | SKVNISPTI | 10676 | 34 |

TABLE 3b

HLA-A24 binding 10 mer peptides derived from NEIL3

| Start Position | Amino acid sequence | Kd (nM) | SEQ ID NO |
|---|---|---|---|
| 320 | HWTCVVCTLI | 195 | 35 |
| 361 | HLMKYPCNTF | 6226 | 36 |
| 257 | CHCRITVCRF | 10173 | 37 |
| 319 | EHWTCVVCTL | 13366 | 38 |
| 568 | IGPNNGKNFF | 14846 | 39 |
| 122 | QLTKDLICFF | 15324 | 40 |
| 544 | FEWADLSFPF | 18029 | 41 |
| 534 | PLPREAQCGF | 19346 | 42 |
| 87 | FGPKALRIHF | 21307 | 43 |

Start position indicates the number of amino acid residue from the N-terminus of NEIL3.
Dissociation constant [Kd (nM)] are derived from "NetMHC3.0".

CTL Induction with the Predicted Peptides from NEIL3 Restricted with HLA-A*2402

CTLs for those peptides derived from NEIL3 were generated according to the protocols as described in "Materials and Methods". Peptide specific CTL activity was determined by IFN-gamma ELISPOT assay (FIGS. 6a-e). It showed that the well number #7 stimulated with NEIL3-A24-9-545 (SEQ ID NO: 24) (a), #6 stimulated with NEIL3-A24-9-362 (SEQ ID NO: 33) (b), #2 and #8 stimulated with NEIL3-A24-10-320 (SEQ ID NO: 35) (c), #8 stimulated with NEIL3-A24-10-544 (SEQ ID NO: 41) (d) and #1 and #4 stimulated with NEIL3-A24-10-87 (SEQ ID NO: 43) (e) demonstrated potent IFN-gamma production as compared to the control wells. On the other hand, no specific CTL activity was determined by stimulation with other peptides shown in Tables 3a and 3b, despite those peptide had possible binding activity with HLA-A*2402. For example, typical negative data of CTL response stimulated with NEIL3-A24-9-364 (SEQ ID NO: 25) against peptide-pulsed target cells (f). As a result, it indicated that 5 peptides derived from NEIL3 were screened as the peptides that could induce potent CTLs.

Establishment of CTL Lines and Clones Against NEIL3 Derived Peptide

The cells that showed peptide specific CTL activity detected by IFN-gamma ELISPOT assay in the well number #7 with NEIL3-A24-9-545 (SEQ ID NO:24) (a), #6 with NEIL3-A24-9-362 (SEQ ID NO: 33) (b), #8 with NEIL3-A24-10-320 (SEQ ID NO: 35) (c), #8 with NEIL3-A24-10-544 (SEQ ID NO: 41) (d) and #1 with NEIL3-A24-10-87 (SEQ ID NO: 43) (e) were expanded and established CTL lines. CTL activity of those CTL lines was determined by IFN-gamma ELISA assay (FIGS. 7a-e). It showed that all CTL lines demonstrated potent IFN-gamma production against the target cells pulsed with corresponding peptide as compared to target cells without peptide pulse. Furthermore, CTL clones were established by limiting dilution from the CTL lines, and IFN-gamma production from CTL clones against target cells pulsed peptide was determined by IFN-gamma ELISA assay. Potent IFN-gamma productions were determined from CTL clones stimulated with NEIL3-A24-9-545 (SEQ ID NO: 24) (a), NEIL3-A24-10-320 (SEQ ID NO: 35) (b) and NEIL3-A24-10-544 (SEQ ID NO: 41) (c) in FIG. 8.

Specific Ctl Activity Against Target Cells Exogenously Expressing NEIL3 and HLA-A*2402

The established CTL lines and clones raised against each peptides were examined for their ability to recognize target cells that endogenously express NEIL3 and HLA-A*2402 gene. Specific CTL activity against COS7 cells which transfected with both the full length of NEIL3 and HLA-A*2402 gene (a specific model for the target cells that exogenously express NEIL3 and HLA-A*2402 gene) was tested using the CTL lines and clones raised by corresponding peptide as the effector cells. COS7 cells transfected with either full length of NEIL3 genes or HLA-A* 2402 were prepared as controls. In FIG. 9, the CTLs stimulated with NEIL3-A24-9-545 (SEQ ID NO: 24) showed potent CTL activity against COS7 cells expressing both NEIL3 and HLA-A*2402. On the other hand, no significant specific CTL activity was detected against the control. Thus, these data clearly demonstrated that NEIL3-A24-9-545 (SEQ ID NO: 24) was naturally expressed on the target cells with HLA-A*2402 molecule and were recognized by the CTLs. These results indicated that this peptide derived from NEIL3 may be available to apply the cancer vaccines for patients with NEIL3 expressing tumors.

Homology Analysis of Antigen Peptides

The CTLs stimulated with NEIL3-A24-9-545 (SEQ ID NO: 24), NEIL3-A24-9-362 (SEQ ID NO: 33), NEIL3-A24-10-320 (SEQ ID NO: 35), NEIL3-A24-10-544 (SEQ ID NO: 41) and NEIL3-A24-10-87 (SEQ ID NO: 43) showed significant and specific CTL activity. This result may be due to the fact that the sequence of NEIL3-A24-9-545 (SEQ ID NO: 24), NEIL3-A24-9-362 (SEQ ID NO: 33), NEIL3-A24-10-320 (SEQ ID NO: 35), NEIL3-A24-10-544 (SEQ ID NO: 41) and NEIL3-A24-10-87 (SEQ ID NO: 43) are homologous to peptide derived from other molecules that are known to sensitize the human immune system. To exclude this possibility, homology analyses were performed for this peptide sequence using as queries the BLAST algorithm (www.ncbi.nlm.nih.gov/blast/blast.cgi) which revealed no sequence with significant homology. The results of homology analyses indicate that the sequence of NEIL3-A24-9-545 (SEQ ID NO: 24), NEIL3-A24-9-362 (SEQ ID NO: 33), NEIL3-A24-10-320 (SEQ ID NO: 35), NEIL3-A24-10-544 (SEQ ID NO: 41) and NEIL3-A24-10-87 (SEQ ID NO: 43) are unique and thus, there is little possibility, to our best knowledge, that this molecules raise unintended immunologic response to some unrelated molecule.

In conclusion, novel HLA-A*2402 epitope peptide derived from NEIL3 are identified. Furthermore, it was demonstrated that NEIL3 may be applicable for cancer immunotherapy.

Industrial Applicability

The present invention provides new TAAs, particularly those derived from NEIL3 which may induce potent and specific anti-tumor immune responses and have applicability to a wide variety of cancer types. Such TAAs can find use in the diagnosis and treatment of cancer.

The invention claimed is:

1. A method of inducing an immune response against cancer overexpressing NEIL3 in a subject, the method comprising administering to the subject a composition comprising a peptide selected from the group consisting of:
   (a) an isolated peptide of less than 15 amino acids comprising the amino acid sequence of SEQ ID NO: 5;
   (b) an isolated peptide consisting of an amino acid sequence of SEQ ID NO: 5, in which 1 or 2 amino acid(s) are substituted, deleted, or added, wherein the peptide has CTL inducibility.

2. The method of claim 1, wherein the cancer is selected from the group consisting of bladder cancer, breast cancer, cervical cancer, cholangiocellular carcinoma, colorectal cancer, endometriosis, esophagus cancer, liver cancer, NSCLC, osteosarcoma, pancreatic cancer, prostate cancer, renal carcinoma, SCLC, soft tissue tumor, AML and CML.

3. The method of claim 1, wherein the wherein the dosage of the peptide is 0.1 mg to 10 mg.

4. The method of claim 1, wherein the peptide is administered in combination with an adjuvant.

5. The method of claim 4, wherein the adjuvant is incomplete Freund's adjuvant.

6. The method of claim 1, wherein the peptide is administered by subcutaneous injection.

7. The method of claim 1, wherein the peptide consists of the amino acid sequence of SEQ ID NO: 5.

8. The method of claim 1, wherein the peptide has one or both of the following characteristics:
   (a) the second amino acid from the N-terminus of the amino acid sequence of SEQ ID NO: 5 is substituted with leucine or methionine; and
   (b) the C-terminal amino acid of the amino acid sequence of SEQ ID NO: 5 is substituted with leucine.

* * * * *

SEQUENCE LISTING

```
<160> NUMBER OF SEQ ID NOS: 51

<210> SEQ ID NO 1
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 1

Val Leu Ser Leu Phe Asn Gly Tyr Val
1               5

<210> SEQ ID NO 2
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 2

Phe Met Tyr Phe Gly Pro Lys Ala Leu
1               5

<210> SEQ ID NO 3
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 3

Lys Gln Cys Asn Phe Phe Gln Trp Ala
1               5

<210> SEQ ID NO 4
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 4

Leu Ile Cys Phe Phe Asp Ser Ser Val
1               5

<210> SEQ ID NO 5
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 5

Phe Gln Asn Ser Pro Pro Ala Ser Val
1               5

<210> SEQ ID NO 6
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 6

Tyr Val Tyr Ser Gly Val Glu Thr Leu
1               5
```

```
<210> SEQ ID NO 7
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 7

Arg Leu Ala Ala Ser Thr Val Val Val
1               5

<210> SEQ ID NO 8
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 8

Ser Leu Gln Gly Arg Ala Leu Arg Leu
1               5

<210> SEQ ID NO 9
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 9

Ile Ile Ser Trp Thr Ser Ser Arg Val
1               5

<210> SEQ ID NO 10
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 10

Lys Leu Pro Thr Arg Asn Thr Ile Ile
1               5

<210> SEQ ID NO 11
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 11

Arg Met Thr Tyr Phe Cys Pro His Cys
1               5

<210> SEQ ID NO 12
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 12

Asn Met Thr Asp Gly Pro Arg Thr Leu
1               5
```

<210> SEQ ID NO 13
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 13

```
Val Leu Pro Gly Gln Ala Val Thr Gly Val
1               5                   10
```

<210> SEQ ID NO 14
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 14

```
Gln Leu Thr Asp Glu Gln Ile His His Leu
1               5                   10
```

<210> SEQ ID NO 15
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 15

```
Ala Leu Phe Asp Ser Gly Leu His Pro Ala
1               5                   10
```

<210> SEQ ID NO 16
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 16

```
Leu Met Asp Gln Asn Val Leu Pro Gly Val
1               5                   10
```

<210> SEQ ID NO 17
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 17

```
Cys Leu Thr Ser Arg Pro Ile Asp Ser Val
1               5                   10
```

<210> SEQ ID NO 18
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 18

```
Gly Leu Ala Leu Ser Lys His Tyr Lys Val
1               5                   10
```

```
<210> SEQ ID NO 19
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 19

Ala Leu Asn Asn Asp Ser Ser Gln Asn Val
1               5                   10

<210> SEQ ID NO 20
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 20

Asn Val Leu Ser Leu Phe Asn Gly Tyr Val
1               5                   10

<210> SEQ ID NO 21
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 21

Phe Gln Trp Ala Glu Asn Gly Pro Gly Ile
1               5                   10

<210> SEQ ID NO 22
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 22

Lys Ile Asn Arg Lys Thr Ala Phe Gly Thr
1               5                   10

<210> SEQ ID NO 23
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 23

Gly Pro Asn Asn Gly Lys Asn Phe Phe Val
1               5                   10

<210> SEQ ID NO 24
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 24

Glu Trp Ala Asp Leu Ser Phe Pro Phe
1               5

<210> SEQ ID NO 25
```

```
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 25

Lys Tyr Pro Cys Asn Thr Phe Gly Lys
1               5

<210> SEQ ID NO 26
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 26

His Trp Thr Cys Val Val Cys Thr Leu
1               5

<210> SEQ ID NO 27
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 27

Tyr Phe Gly Pro Lys Ala Leu Arg Ile
1               5

<210> SEQ ID NO 28
<211> LENGTH: 9
<212> TYPE: PRT
<213> ORGANISM: Artichoke mottled crinkle virus

<400> SEQUENCE: 28

Ser Ser Gln Asn Val Leu Ser Leu Phe
1               5

<210> SEQ ID NO 29
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 29

Gln Trp Ala Glu Asn Gly Pro Gly Ile
1               5

<210> SEQ ID NO 30
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 30

Ser Thr Met Lys Thr Val Leu Lys Ile
1               5

<210> SEQ ID NO 31
<211> LENGTH: 9
<212> TYPE: PRT
<213> ORGANISM: Artificial Sequence
```

<220> FEATURE:
<223> OTHER INFORMATION: an artificially synthesized peptide sequence

<400> SEQUENCE: 31

Asn Ile Ile Lys Asn Glu Ala Leu Phe
1               5

<210> SEQ ID NO 32
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 32

Val Leu Pro Gly Val Gly Asn Ile Ile
1               5

<210> SEQ ID NO 33
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 33

Leu Met Lys Tyr Pro Cys Asn Thr Phe
1               5

<210> SEQ ID NO 34
<211> LENGTH: 9
<212> TYPE: PRT
<213> ORGANISM: Artificial Sequence
<220> FEATURE:
<223> OTHER INFORMATION: an artificially synthesized peptide sequence

<400> SEQUENCE: 34

Ser Lys Val Asn Ile Ser Pro Thr Ile
1               5

<210> SEQ ID NO 35
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 35

His Trp Thr Cys Val Val Cys Thr Leu Ile
1               5                   10

<210> SEQ ID NO 36
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 36

His Leu Met Lys Tyr Pro Cys Asn Thr Phe
1               5                   10

<210> SEQ ID NO 37
<211> LENGTH: 10
<212> TYPE: PRT
<213> ORGANISM: Artificial Sequence
<220> FEATURE:

<223> OTHER INFORMATION: an artificially synthesized peptide sequence

<400> SEQUENCE: 37

Cys His Cys Arg Ile Thr Val Cys Arg Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 38

Glu His Trp Thr Cys Val Val Cys Thr Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 39

Ile Gly Pro Asn Asn Gly Lys Asn Phe Phe
1               5                   10

<210> SEQ ID NO 40
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 40

Gln Leu Thr Lys Asp Leu Ile Cys Phe Phe
1               5                   10

<210> SEQ ID NO 41
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 41

Phe Glu Trp Ala Asp Leu Ser Phe Pro Phe
1               5                   10

<210> SEQ ID NO 42
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 42

Pro Leu Pro Arg Glu Ala Gln Cys Gly Phe
1               5                   10

<210> SEQ ID NO 43
<211> LENGTH: 10
<212> TYPE: PRT
<213> ORGANISM: Artificial Sequence
<220> FEATURE:
<223> OTHER INFORMATION: an artificially synthesized peptide sequence

<400> SEQUENCE: 43

Phe Gly Pro Lys Ala Leu Arg Ile His Phe
1               5                   10

<210> SEQ ID NO 44
<211> LENGTH: 2402
<212> TYPE: DNA
<213> ORGANISM: Homo sapiens
<220> FEATURE:
<221> NAME/KEY: CDS
<222> LOCATION: (118)..(1935)

<400> SEQUENCE: 44

```
gacgcgcgcg agatttgaat ttcctctgcg tgcggtcagt gcccgcgcag cgttgagttg      60
cacagcggta ttctcaccag gccctgcaat cggtgggcca cagtgccggc cacagag       117 atg gtg gaa gga cca ggc tgt act ctg aat gga gag aag att cgc gcg     165
Met Val Glu Gly Pro Gly Cys Thr Leu Asn Gly Glu Lys Ile Arg Ala
1               5                   10                  15 cgg gtg ctc ccg ggc cag gcg gtg acc ggc gtg cgg gga agc gct ctg     213
Arg Val Leu Pro Gly Gln Ala Val Thr Gly Val Arg Gly Ser Ala Leu
                20                  25                  30 cgg agt ctg cag ggc cgc gcc ttg cgg ctc gca gcc tcc acg gtt gtg     261
Arg Ser Leu Gln Gly Arg Ala Leu Arg Leu Ala Ala Ser Thr Val Val
            35                  40                  45 gtc tcc ccg cag gct gct gca ctg aat aat gat tcc agc cag aat gtc     309
Val Ser Pro Gln Ala Ala Ala Leu Asn Asn Asp Ser Ser Gln Asn Val
        50                  55                  60 ttg agc ctg ttt aat gga tat gtt tac agt ggc gtg gaa act ttg ggg     357
Leu Ser Leu Phe Asn Gly Tyr Val Tyr Ser Gly Val Glu Thr Leu Gly
65                  70                  75                  80 aag gag ctc ttt atg tac ttt gga cca aaa gct tta cgg att cat ttc     405
Lys Glu Leu Phe Met Tyr Phe Gly Pro Lys Ala Leu Arg Ile His Phe
                85                  90                  95 gga atg aaa ggc ttc atc atg att aat cca ctt gag tat aaa tat aaa     453
Gly Met Lys Gly Phe Ile Met Ile Asn Pro Leu Glu Tyr Lys Tyr Lys
                100                 105                 110 aat gga gct tct cct gtt ttg gaa gtg cag ctc acc aaa gat ttg att     501
Asn Gly Ala Ser Pro Val Leu Glu Val Gln Leu Thr Lys Asp Leu Ile
            115                 120                 125 tgt ttc ttt gac tca tca gta gaa ctc aga aac tca atg gaa agc caa     549
Cys Phe Phe Asp Ser Ser Val Glu Leu Arg Asn Ser Met Glu Ser Gln
        130                 135                 140 cag aga ata aga atg atg aaa gaa tta gat gta tgt tca cct gaa ttt     597
Gln Arg Ile Arg Met Met Lys Glu Leu Asp Val Cys Ser Pro Glu Phe
145                 150                 155                 160 agt ttc ttg aga gca gaa agt gaa gtt aaa aaa cag aaa ggc cgg atg     645
Ser Phe Leu Arg Ala Glu Ser Glu Val Lys Lys Gln Lys Gly Arg Met
                165                 170                 175 cta ggt gat gtg cta atg gat cag aac gta ttg cct gga gta ggg aac     693
Leu Gly Asp Val Leu Met Asp Gln Asn Val Leu Pro Gly Val Gly Asn
                180                 185                 190 atc atc aaa aat gaa gct ctc ttt gac agt ggt ctc cac cca gct gtt     741
Ile Ile Lys Asn Glu Ala Leu Phe Asp Ser Gly Leu His Pro Ala Val
            195                 200                 205 aaa gtt tgt caa tta aca gat gaa cag atc cat cac ctc atg aaa atg     789
Lys Val Cys Gln Leu Thr Asp Glu Gln Ile His His Leu Met Lys Met
        210                 215                 220 ata cgt gat ttc agc att ctc ttt tac agg tgc cgt aaa gca gga ctt     837
Ile Arg Asp Phe Ser Ile Leu Phe Tyr Arg Cys Arg Lys Ala Gly Leu
```

```
                      225                 230                 235                 240
gct ctc tct aaa cac tat aag gtt tac aag cgt cct aat tgt ggt cag        885
Ala Leu Ser Lys His Tyr Lys Val Tyr Lys Arg Pro Asn Cys Gly Gln
                245                 250                 255 tgc cac tgc aga ata act gtg tgc cgc ttt ggg gac aat aac aga atg        933
Cys His Cys Arg Ile Thr Val Cys Arg Phe Gly Asp Asn Asn Arg Met
            260                 265                 270 aca tat ttc tgt cct cac tgt caa aaa gaa aat cct caa cat gtt gac        981
Thr Tyr Phe Cys Pro His Cys Gln Lys Glu Asn Pro Gln His Val Asp
        275                 280                 285 ata tgc aag cta ccg act aga aat act ata atc agt tgg aca tct agc       1029
Ile Cys Lys Leu Pro Thr Arg Asn Thr Ile Ile Ser Trp Thr Ser Ser
    290                 295                 300 agg gtg gat cat gtt atg gac tcc gtg gct cgg aag tcg gaa gag cac       1077
Arg Val Asp His Val Met Asp Ser Val Ala Arg Lys Ser Glu Glu His
305                 310                 315                 320 tgg acc tgt gtg gtg tgt act tta atc aat aag ccc tct tct aag gca       1125
Trp Thr Cys Val Val Cys Thr Leu Ile Asn Lys Pro Ser Ser Lys Ala
                325                 330                 335 tgt gat gct tgc ttg acc tca agg cct att gat tca gtg ctc aag agt       1173
Cys Asp Ala Cys Leu Thr Ser Arg Pro Ile Asp Ser Val Leu Lys Ser
            340                 345                 350 gaa gaa aat tct act gtc ttt agc cac tta atg aag tac ccg tgt aat       1221
Glu Glu Asn Ser Thr Val Phe Ser His Leu Met Lys Tyr Pro Cys Asn
        355                 360                 365 act ttt gga aaa cct cat aca gaa gtc aag atc aac aga aaa act gca       1269
Thr Phe Gly Lys Pro His Thr Glu Val Lys Ile Asn Arg Lys Thr Ala
    370                 375                 380 ttt gga act aca act ctt gtc ttg act gat ttt agc aat aaa tcc agt       1317
Phe Gly Thr Thr Thr Leu Val Leu Thr Asp Phe Ser Asn Lys Ser Ser
385                 390                 395                 400 act ttg gaa aga aaa aca aag caa aac cag ata cta gat gag gag ttt       1365
Thr Leu Glu Arg Lys Thr Lys Gln Asn Gln Ile Leu Asp Glu Glu Phe
                405                 410                 415 caa aac tct cct cct gct agt gtt tgt ttg aat gat ata cag cac ccc       1413
Gln Asn Ser Pro Pro Ala Ser Val Cys Leu Asn Asp Ile Gln His Pro
            420                 425                 430 tcc aag aag aca aca aac gat ata act caa cca tcc agc aaa gta aac       1461
Ser Lys Lys Thr Thr Asn Asp Ile Thr Gln Pro Ser Ser Lys Val Asn
        435                 440                 445 ata tca cct aca atc agt tca gaa tct aaa tta ttt agt cca gca cat       1509
Ile Ser Pro Thr Ile Ser Ser Glu Ser Lys Leu Phe Ser Pro Ala His
    450                 455                 460 aaa aaa ccg aaa aca gcc caa tac tca tca cca gag ctt aaa agc tgc       1557
Lys Lys Pro Lys Thr Ala Gln Tyr Ser Ser Pro Glu Leu Lys Ser Cys
465                 470                 475                 480 aac cct gga tat tct aac agt gaa ctt caa att aat atg aca gat ggc       1605
Asn Pro Gly Tyr Ser Asn Ser Glu Leu Gln Ile Asn Met Thr Asp Gly
                485                 490                 495 cct cgt acc tta aat cct gac agc cct cgc tgc agt aaa cac aac cgc       1653
Pro Arg Thr Leu Asn Pro Asp Ser Pro Arg Cys Ser Lys His Asn Arg
            500                 505                 510 ctc tgc att ctc cga gtt gtg agg aag gat ggg gaa aac aag ggc agg       1701
Leu Cys Ile Leu Arg Val Val Arg Lys Asp Gly Glu Asn Lys Gly Arg
        515                 520                 525 cag ttt tat gcc tgt cct cta cct aga gaa gca caa tgt gga ttt ttt       1749
Gln Phe Tyr Ala Cys Pro Leu Pro Arg Glu Ala Gln Cys Gly Phe Phe
    530                 535                 540 gaa tgg gca gat ttg tcc ttc cca ttc tgc aac cat ggc aag cgt tcc       1797
Glu Trp Ala Asp Leu Ser Phe Pro Phe Cys Asn His Gly Lys Arg Ser
```

-continued

```
Glu Trp Ala Asp Leu Ser Phe Pro Phe Cys Asn His Gly Lys Arg Ser
545                 550                 555                 560 acc atg aaa aca gta ttg aag att gga cct aac aat gga aag aat ttt      1845
Thr Met Lys Thr Val Leu Lys Ile Gly Pro Asn Asn Gly Lys Asn Phe
                565                 570                 575 ttt gtg tgt cct ctt ggg aag gaa aaa caa tgc aat ttt ttc cag tgg      1893
Phe Val Cys Pro Leu Gly Lys Glu Lys Gln Cys Asn Phe Phe Gln Trp
            580                 585                 590 gca gaa aat ggg cca gga ata aaa att att cct gga tgc taa              1935
Ala Glu Asn Gly Pro Gly Ile Lys Ile Ile Pro Gly Cys
        595                 600                 605 tatctgtaga ttctctggca tttagtctct tcaaactgtg tataatgttt ggtcctcctc    1995
tgtttcatag aaaagtcata gaatatctat gatacattga aaagttactg caatatttga    2055
gaactgttct ttttttttct tgtgtgtgcc atctttccat tgttggctac gtcttttctt    2115
ttgccttgat gaacgttcta tgtatttcat cggatataca gcatattcca tttaggatgt    2175
gtatttaatg catttagtaa tgacgataaa gtgttttag tatgctttta gtctcttgta    2235
actggggaga agcagtgttt ttttttagg aaaggattat gcgacacaat aaaataagat    2295
attctgtctg tagtgaatac atttctcatg tactaacact atttataata tatgattaaa    2355
gatatttctt gttttattaa ataataagaa ataagatctc ctttatg                  2402
```

<210> SEQ ID NO 45
<211> LENGTH: 605
<212> TYPE: PRT
<213> ORGANISM: Homo sapiens

<400> SEQUENCE: 45

```
Met Val Glu Gly Pro Gly Cys Thr Leu Asn Gly Glu Lys Ile Arg Ala
1               5                   10                  15

Arg Val Leu Pro Gly Gln Ala Val Thr Gly Val Arg Gly Ser Ala Leu
                20                  25                  30

Arg Ser Leu Gln Gly Arg Ala Leu Arg Leu Ala Ala Ser Thr Val Val
            35                  40                  45

Val Ser Pro Gln Ala Ala Ala Leu Asn Asn Asp Ser Ser Gln Asn Val
        50                  55                  60

Leu Ser Leu Phe Asn Gly Tyr Val Tyr Ser Gly Val Glu Thr Leu Gly
65                  70                  75                  80

Lys Glu Leu Phe Met Tyr Phe Gly Pro Lys Ala Leu Arg Ile His Phe
                85                  90                  95

Gly Met Lys Gly Phe Ile Met Ile Asn Pro Leu Glu Tyr Lys Tyr Lys
            100                 105                 110

Asn Gly Ala Ser Pro Val Leu Glu Val Gln Leu Thr Lys Asp Leu Ile
        115                 120                 125

Cys Phe Phe Asp Ser Ser Val Glu Leu Arg Asn Ser Met Glu Ser Gln
130                 135                 140

Gln Arg Ile Arg Met Met Lys Glu Leu Asp Val Cys Ser Pro Glu Phe
145                 150                 155                 160

Ser Phe Leu Arg Ala Glu Ser Glu Val Lys Lys Gln Lys Gly Arg Met
                165                 170                 175

Leu Gly Asp Val Leu Met Asp Gln Asn Val Leu Pro Gly Val Gly Asn
            180                 185                 190

Ile Ile Lys Asn Glu Ala Leu Phe Asp Ser Gly Leu His Pro Ala Val
        195                 200                 205

Lys Val Cys Gln Leu Thr Asp Glu Gln Ile His His Leu Met Lys Met
```

```
            210                 215                 220
Ile Arg Asp Phe Ser Ile Leu Phe Tyr Arg Cys Arg Lys Ala Gly Leu
225                 230                 235                 240

Ala Leu Ser Lys His Tyr Lys Val Tyr Lys Arg Pro Asn Cys Gly Gln
                245                 250                 255

Cys His Cys Arg Ile Thr Val Cys Arg Phe Gly Asp Asn Asn Arg Met
            260                 265                 270

Thr Tyr Phe Cys Pro His Cys Gln Lys Glu Asn Pro Gln His Val Asp
        275                 280                 285

Ile Cys Lys Leu Pro Thr Arg Asn Thr Ile Ile Ser Trp Thr Ser Ser
    290                 295                 300

Arg Val Asp His Val Met Asp Ser Val Ala Arg Lys Ser Glu Glu His
305                 310                 315                 320

Trp Thr Cys Val Val Cys Thr Leu Ile Asn Lys Pro Ser Ser Lys Ala
                325                 330                 335

Cys Asp Ala Cys Leu Thr Ser Arg Pro Ile Asp Ser Val Leu Lys Ser
            340                 345                 350

Glu Glu Asn Ser Thr Val Phe Ser His Leu Met Lys Tyr Pro Cys Asn
        355                 360                 365

Thr Phe Gly Lys Pro His Thr Glu Val Lys Ile Asn Arg Lys Thr Ala
    370                 375                 380

Phe Gly Thr Thr Thr Leu Val Leu Thr Asp Phe Ser Asn Lys Ser Ser
385                 390                 395                 400

Thr Leu Glu Arg Lys Thr Lys Gln Asn Gln Ile Leu Asp Glu Phe
                405                 410                 415

Gln Asn Ser Pro Pro Ala Ser Val Cys Leu Asn Asp Ile Gln His Pro
            420                 425                 430

Ser Lys Lys Thr Thr Asn Asp Ile Thr Gln Pro Ser Ser Lys Val Asn
        435                 440                 445

Ile Ser Pro Thr Ile Ser Ser Glu Ser Lys Leu Phe Ser Pro Ala His
    450                 455                 460

Lys Lys Pro Lys Thr Ala Gln Tyr Ser Ser Pro Glu Leu Lys Ser Cys
465                 470                 475                 480

Asn Pro Gly Tyr Ser Asn Ser Glu Leu Gln Ile Asn Met Thr Asp Gly
                485                 490                 495

Pro Arg Thr Leu Asn Pro Asp Ser Pro Arg Cys Ser Lys His Asn Arg
            500                 505                 510

Leu Cys Ile Leu Arg Val Val Arg Lys Asp Gly Glu Asn Lys Gly Arg
        515                 520                 525

Gln Phe Tyr Ala Cys Pro Leu Pro Arg Glu Ala Gln Cys Gly Phe Phe
    530                 535                 540

Glu Trp Ala Asp Leu Ser Phe Pro Phe Cys Asn His Gly Lys Arg Ser
545                 550                 555                 560

Thr Met Lys Thr Val Leu Lys Ile Gly Pro Asn Asn Gly Lys Asn Phe
                565                 570                 575

Phe Val Cys Pro Leu Gly Lys Glu Lys Gln Cys Asn Phe Phe Gln Trp
            580                 585                 590

Ala Glu Asn Gly Pro Gly Ile Lys Ile Ile Pro Gly Cys
        595                 600                 605

<210> SEQ ID NO 46
<211> LENGTH: 23
<212> TYPE: DNA
<213> ORGANISM: Artificial
```

```
<220> FEATURE:
<223> OTHER INFORMATION: an artificially synthesized primer sequence

<400> SEQUENCE: 46
ttggtcctcc tctgtttcat aga                                           23

<210> SEQ ID NO 47
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 47
gcttctcccc agttacaaga gac                                           23

<210> SEQ ID NO 48
<211> LENGTH: 22
<212> TYPE: DNA
<213> ORGANISM: Artificial Sequence
<220> FEATURE:
<223> OTHER INFORMATION: Artificial sequence

<400> SEQUENCE: 48
gtctaccagg cattcgcttc at                                            22

<210> SEQ ID NO 49
<211> LENGTH: 24
<212> TYPE: DNA
<213> ORGANISM: Artificial Sequence
<220> FEATURE:
<223> OTHER INFORMATION: Artificial sequence

<400> SEQUENCE: 49
tcagctggac cacagccgca gcgt                                          24

<210> SEQ ID NO 50
<211> LENGTH: 21
<212> TYPE: DNA
<213> ORGANISM: Artificial Sequence
<220> FEATURE:
<223> OTHER INFORMATION: Artificial sequence

<400> SEQUENCE: 50
tcagaaatcc tttctcttga c                                             21

<210> SEQ ID NO 51
<211> LENGTH: 24
<212> TYPE: DNA
<213> ORGANISM: Artificial Sequence
<220> FEATURE:
<223> OTHER INFORMATION: Artificial sequence

<400> SEQUENCE: 51
ctagcctctg gaatcctttc tctt                                          24
```